(12) United States Patent
Yang et al.

(10) Patent No.: US 8,323,750 B2
(45) Date of Patent: Dec. 4, 2012

(54) METHOD OF ULTRAVIOLET LIGHT ASSISTED SURFACE MODIFICATION AND PRODUCT HAVING A SURFACE FORMED BY THIS METHOD

(75) Inventors: Wantai Yang, Beijing (CN); Zhenhua Huang, Beijing (CN); Yanhe Tong, Fremont, CA (US); Lei Shao, Beijing (CN)

(73) Assignees: Beijing Wanhexinyuan BioTechnology Co., Ltd., Beijing (CN); Beijing University of Chemical Technology, Beijing (CN)

( * ) Notice: Subject to any disclaimer, the term of this patent is extended or adjusted under 35 U.S.C. 154(b) by 208 days.

(21) Appl. No.: 12/672,048

(22) PCT Filed: Aug. 20, 2008

(86) PCT No.: PCT/CN2008/072065
§ 371 (c)(1),
(2), (4) Date: Feb. 3, 2010

(87) PCT Pub. No.: WO2009/024087
PCT Pub. Date: Feb. 26, 2009

(65) Prior Publication Data
US 2011/0124766 A1    May 26, 2011

(30) Foreign Application Priority Data

Aug. 21, 2007 (CN) .......................... 2007 1 0146564

(51) Int. Cl.
*C08F 2/50* (2006.01)
*C08J 3/28* (2006.01)
*C07D 311/86* (2006.01)

(52) U.S. Cl. ........ 427/517; 427/508; 427/513; 427/523; 427/533; 427/536; 522/33; 522/34; 522/35; 522/904; 522/135; 522/134; 522/141; 522/143; 522/113; 522/114; 522/120; 522/122; 522/149; 522/150; 522/162; 210/500.21; 210/500.27; 210/506; 549/390; 549/388; 549/392; 549/393

(58) Field of Classification Search ................ 522/33, 522/34, 35, 904, 135, 134, 141, 143, 113, 522/114, 120, 122, 149, 150, 162; 427/508, 427/513, 517, 532, 533, 536; 210/500.21, 210/500.27, 506; 549/30, 388, 392, 393
See application file for complete search history.

(56) References Cited

U.S. PATENT DOCUMENTS

| 4,979,959 | A | 12/1990 | Guire ............................ 623/66 |
| 5,310,909 | A | 5/1994 | Fischer et al. ................ 546/41 |
| 5,977,077 | A | 11/1999 | Winter et al. ................. 514/23 |
| 7,138,541 | B2 * | 11/2006 | Swan ............................ 562/53 |
| 2004/0101442 | A1 | 5/2004 | Frechet et al. ................ 422/99 |
| 2010/0206806 | A1 * | 8/2010 | Waller et al. ............ 210/500.35 |

FOREIGN PATENT DOCUMENTS

| CN | 85107319 | 4/1987 |
| CN | 1431206 | 7/2003 |
| CN | 1449399 | 10/2003 |
| CN | 1607213 | 4/2005 |
| WO | WO 2007/070761 | 6/2007 |

OTHER PUBLICATIONS

Arthur P. van der Heiden et al., "A photochemical method for the surface modification of poly (etherurethanes) with phosphorylcholine-containing compounds to improve hemocompatibility" Journal of biomedical materials research, John Wiley & Sons, New York, NY, 1997, vol. 37, n°2, pp. 282-290.

Chinese Second Examination Report in corresponding to China Application No. 200710146564.6, dated on Sep. 27, 2011.

* cited by examiner

*Primary Examiner* — Sanza McClendon
(74) *Attorney, Agent, or Firm* — J.C. Patents

(57) ABSTRACT

The present invention relates to a UV irradiation assisted method of surface modification, which comprises: introducing a functional group L onto the surface of a polymer material P through the photochemical reaction of a photosensitive group X under UV irradiation, wherein the photosensitive group X comprises at least one xanthone unit.

50 Claims, 2 Drawing Sheets

METHOD OF ULTRAVIOLET LIGHT ASSISTED SURFACE MODIFICATION AND PRODUCT HAVING A SURFACE FORMED BY THIS METHOD

FIELD OF THE INVENTION

The present invention relates to a method for surface modification, particularly, a method for the modification of polymer surfaces with the assistance of ultraviolet light, and a modification compound for use in the ultraviolet light assisted surface modification, as well as articles having a surface modified by this method.

BACKGROUND OF THE INVENTION

Materials having special surface properties are widely used in printing, dyeing, bonding, blocking and biological fields etc. For example, polyethylene terephthalate (PET) films having good surface hydrophilicity have good coloring properties, and may be used to print packing materials with various colors and patterns; polymer materials having good surface biological properties may be widely used in fields such as biosensor, medical biological material and biological fast detection.

Generally, materials having different surface properties may be obtained by surface modification. The methods include wet chemical method, chemical etching, corona method, plasma method, high-energy radiation and photochemical method, etc.

UV Initiated Surface Photografting is a photochemical method that immobilizes modification molecules on the surface of materials by covalent bonding with the assistance of UV radiation, so as to achieve the objective of modification. With UV irradiation, the modification molecule is covalently linked to the surface of the materials through surface graft polymerization (polymerization method) or surface coupling (coupling method). The UV coupling method achieves the surface linkage of functional groups and the surface of materials through the bridging action of photosensitive groups, and materials having different surface properties may be obtained by altering the functional groups.

In recent years, the method of polymer surface modification by introducing functional groups through UV coupling has aroused researchers' interests.

J. Biomed. Mater. Res. 1997, 37, 282-290 disclosed a surface modification method on polyurethane by modification molecule in which azidobenzene was used as the photosensitive group and phosphorylcholine as the functional group. The disadvantages of this method include: the nitrene free radical produced by UV radiation of azidobenzene group is excessively active, tending to cause side reaction and result in a decreased efficiency of surface modification; in addition, the substance is extremely reactive and may have post or instant reaction with most compounds, organic solvents and water.

WO 96/31557 disclosed a surface modification method to synthesize a series of compounds using quinone compounds as the photosensitive group. The disadvantages of this method include: quinone groups are comparatively weak in photosensitivity, leading to a comparatively longer UV irradiation time, which is not favorable to fast production and cost saving.

Thus, there is a need in this field for modification molecules containing a photosensitive group that can produce free radicals with desired activity and have comparatively strong photosensitivity, for use in ultraviolet light assisted surface modification method.

SUMMARY OF THE INVENTION

The present invention is aimed at providing a method for the modification of surfaces of materials, which can overcome the above-mentioned problems in the prior art. The method comprises introducing functional group L onto the surface of polymer material P by a photochemical reaction of a photosensitive group X comprising at least one xanthone unit under UV irradiation.

A molecule X-L and/or X-S-L can be introduced onto the surface of a polymer material P by the method of the present invention, where X represents a photosensitive group comprising at least one xanthone unit, L represents a functional group, and the S represents a linker.

In an embodiment, the photosensitive group X and the surface of polymer material P link with each other in a way that is selected from P-X-L and P-X-S-L, where the definitions of P, X, L and S are the same as described above.

As for the method of the present invention, the linking arrangements described herein above may be realized through the following routes:

(1) Synthesizing a molecule X-L or X-S-L, and then having the molecule X-L or X-S-L photochemically reacted with the surface of a polymer material P with UV irradiation, thereby introducing the molecule X-L or X-S-L onto the surface of the polymer material P to form P-X-L or a P-X-S-L.

(2) Having a photosensitive group X photochemically reacted with the surface of a polymer material P with UV irradiation to form P-X, and synthesizing a molecule S-L independently, and then linking molecule S-L with the surface of the polymer material P where P-X has been formed, with photochemical or thermochemical reaction, thereby forming P-X-S-L.

(3) Synthesizing a molecule X-S, and then linking molecule X-S to the surface of a polymer material P by photochemical reaction to form P-X-S, followed by linking a functional group L to the surface of the polymer material P where the P-X-S has been formed, with photochemical or thermochemical reaction, thereby forming P-X-S-L.

(4) Fixing a photosensitive group X onto the surface of a polymer material P by photochemical reaction to form P-X, and then optionally linking a linker S through photochemical or thermochemical reaction with the photosensitive group X to form P-X-S, and subsequently linking a functional group L with the photosensitive group X that has been fixed onto the surface of the polymer material P and has been optionally linked with linker S, by photochemical or thermochemical reaction, thereby introducing a molecule X-L or X-S-L onto the surface of the polymer material P to form P-X-L or a P-X-S-L.

With the illustrative description above, those skilled in the art should appreciate that other methods to form P-X-L and P-X-S-L linking arrangements are also included in the scope of the present invention without departing from the spirit of the invention.

In another embodiment, before introducing molecule X-L and/or X-S-L onto the surface of the polymer material P, a linker S' may be fixed onto the surface of the polymer material P to be modified, optionally through photochemical or thermochemical reaction, to form a P-S', and then introducing molecule X-L or X-S-L onto the surface of the polymer material P where the linker S' has been fixed thereon, thereby forming P-S'-X-L or P-S'-X-S-L. $S_i'$ units that composes the linker S' may each independently be the identical or different.

The linker S' may be selected properties with respect to its length, flexibility, reactivity, hydrophobicity/hydrophilicity etc. according to the properties of the surface to be modified. And, the detailed description below on linker S can be consulted for the selection of linker S'. The routes described hereinabove may be realized through different procedures, the first one of which is hereby taken as an example for detailed description.

As for the first route, the modification method may particularly include the following steps:

A. Synthesizing a molecule X-S-L or X-L, where X represents a photosensitive group comprising at least one xanthone unit, L represents a functional group, and S represents a linker;

B. Mixing molecule X-S-L or X-L with a solvent to form a modification solution that contains molecule X-S-L or X-L;

C. Forming a layer of modification solution on the surface of the polymer material P to be modified;

D. Radiating the surface of the polymer material P having the modification solution layer described above with ultraviolet light so as to introduce molecule X-S-L or X-L onto the surface.

If necessary, the method may include E.: after radiation, removing the residual modification molecule from the surface.

The modification molecule X-S-L involved in the modification method may be synthesized by any of the following procedures:

(1) A group X reacts with units $S_i$ that constitutes linker S stepwise till linker S reaches a desired length, to obtain an X-S, which is then linked with a group L to obtain an X-S-L;

(2) Units $S_i$ that constitute linker S react with each other to obtain linker S meeting the length requirement, and then the linker S reacts with a group X to obtain an X-S, which is then linked with a group L to obtain an X-S-L;

(3) Units $S_i$ that constitute linker S react with each other to obtain linker S meeting the length requirement, and then the linker S reacts with a group L to obtain an S-L, which is then linked with a group X to obtain an X-S-L;

(4) A group L reacts with units $S_i$ that constitutes linker S stepwise till linker S reaches a desired length, to obtain an S-L, which is then linked with a group X to obtain an X-S-L.

In the synthetic processes described above, the linking of group X with linker S, extension of linker S, and the linking of linker S with group L can be achieved by thermochemical or photochemical reaction (including microwave radiation chemistry), etc. $S_i$ units that constitute linker S may each independently be the identical or different.

The modification molecule X-L involved in the modification methods may be obtained by reaction between group X and group L. In the synthetic processes described above, the linking of group X with group L can be achieved by thermochemical or photochemical reaction (including microwave radiation chemistry), etc.

The photosensitive group X involved herein comprises at least one xanthone unit. For example, the photosensitive group X may be originated from a substance selected from: substituted or unsubstituted mono-xanthone (e.g. formula 1), substituted or unsubstituted fused ring dixanthone such as 1,4-benzopyronoxanthone (e.g. formula 2) and xanthonoxanthone (e.g. formula 3), substituted or unsubstituted bixanthonyl (e.g. formula 4-7), and substituted or unsubstituted oligomeric xanthone (e.g. formula 8). Preferably, the photosensitive group X is originated from substituted or unsubstituted mono-xanthone.

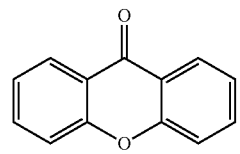

Formula 1

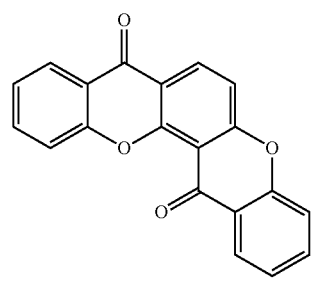

Formula 2

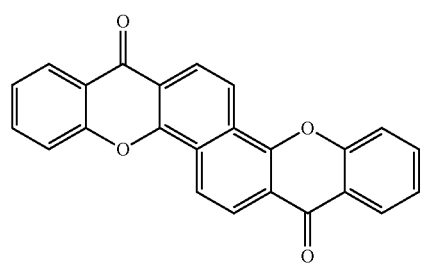

Formula 3

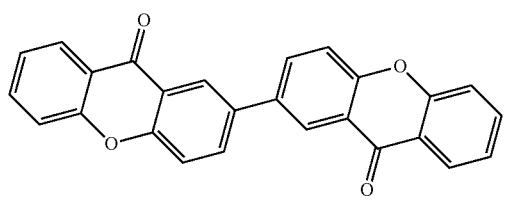

Formula 4

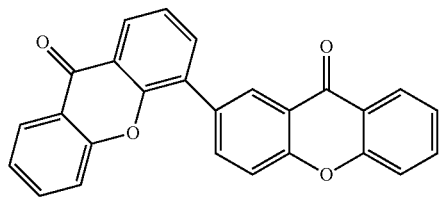

Formula 5

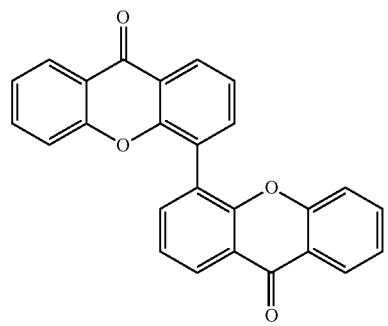

Formula 6

-continued

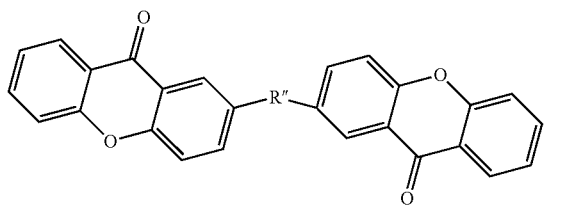

Formula 7

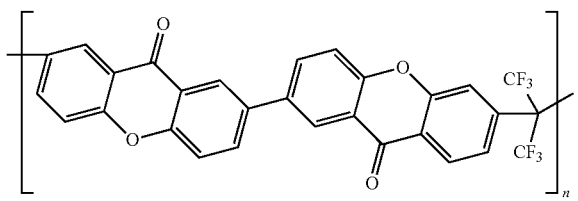

Formula 8

In the bixanthonyl represented by formula 7, R" represents a single bond or a substituted or unsubstituted $C_{1-12}$ alkylene, preferably a substituted or unsubstituted $C_{1-4}$ alkylene, as shown in Formula 9.

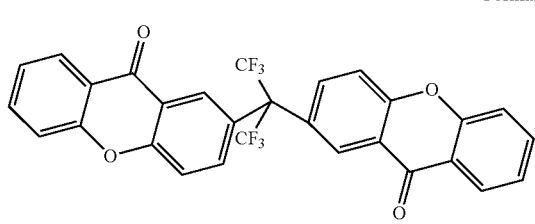

Formula 9

In the present invention, to realize the linking of group X with chain S and group L, the mono-xanthone can be substituted as shown in Formula I:

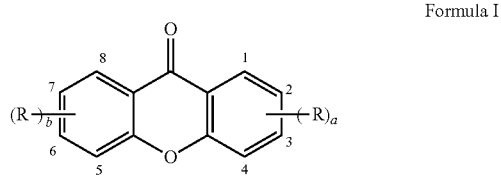

Formula I wherein R independently represents a substituents on the corresponding ring, a and b are independently selected from integers of 0-3, and a+b≧1. Preferably, a and b are independently selected from integers of 0-2, and a+b≧1, and particular preferably a+b=1 or 2.

In Formula I, the substituent R may be a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units. Mono-xanthone without any ring substituent is preferably used as the photosensitive group X in the present method. A detailed description on these cases is given herein below, however, this does not mean that the R is limited to the same type of substituent described above when a plural number of R groups are present, and the separated description is only for convenience.

The thermosensitive functional groups include for example carboxyl groups, hydroxyl groups, amine groups (primary amine group secondary amine group, and tertiary amine group), thiol groups, sulfonic acid groups, halogen atoms, ester groups, acyl halide groups, acid hydrazide groups, semicarbazide groups, thiosemicarbazide groups, aldehyde groups, and ketone groups, wherein the number of carbon atom on backbone is generally no more than 18, preferably no more than 15, particular preferably no more than 8, and even more preferably no more than 5. If the thermosensitive functional groups are present, the photosensitive group X may be derived from for example xanthone-3-acyl chloride, 2-hydroxyl xanthone, 4-hydroxyl xanthone, 2-formyl xanthone, 3-formyl xanthone, 4-formyl-7-hydroxyl xanthone, 3-amino xanthone, etc.

The acyclic hydrocarbyl groups may be a $C_{1-18}$ acyclic hydrocarbyl groups, preferably a $C_{1-8}$ acyclic hydrocarbyl groups, more preferably a $C_{1-5}$ acyclic hydrocarbyl groups, and particular preferably a $C_{1-3}$ acyclic hydrocarbyl groups that may be substituted or unsubstituted and/or interrupted by a functional groups. The term "acyclic hydrocarbyl groups" used herein includes linear and branched ones. According to the present invention, the $C_{1-18}$ acyclic hydrocarbyl groups may be a $C_{1-18}$ alkyl, preferably a $C_{1-8}$ alkyl, more preferably a $C_{1-5}$ alkyl, and particular preferably a $C_{1-3}$ alkyl, such as methyl, ethyl, n-propyl, isopropyl and hexyl; or a $C_{2-18}$ unsaturated hydrocarbyl groups (such as alkenyl, alkynyl), preferably $C_{2-8}$ unsaturated hydrocarbyl groups, more preferably $C_{2-5}$ unsaturated hydrocarbyl groups, and particular preferably $C_{3-5}$ unsaturated hydrocarbyl groups, such as ethenyl, propenyl, n-butenyl, butadienyl, butynyl, pentadienyl, and 2-methyl-2-butenyl.

As described above, the acyclic hydrocarbyl groups may be substituted and/or interrupted by a functional group. For example, the chain substituent may be substituted by one or more of the functional groups selected from below or may be interrupted by one or more of the functional groups selected from below: carboxyl groups, hydroxyl groups, amine groups (primary amine groups, secondary amine groups, and tertiary amine groups, etc.), imine groups, thiol groups, sulfonic acid groups, halogen atoms, ester functional groups, acyl halide groups, acid hydrazide groups, semicarbazide groups, thiosemicarbazide groups, aldehyde groups, and ketone groups, epoxide groups, ether groups, thioether groups, carbonyl groups, sulfonyl groups, sufinyl groups, nitro groups, nitrile groups, phosphoryl functional groups, furan functional groups, carbohydrate functional groups and acyl functional groups. The halogen atoms are for example fluorine, chlorine, bromine, iodine.

When the acyclic hydrocarbyl groups are substituted by the functional groups described above, the examples include but are not limited to 2-aminopropyl, 3-aminoamyl, 2-aminohexenyl; 2-carboxyl-butyl, 4-carboxyl-heptyl, 3-carboxyl-decatyl; hydroxymethyl, hydroxyethyl, hydroxypropyl, dihydroxyamyl; chloromethyl, trifluoromethyl, chlorovinyl, chlorobutadienyl; acrylamide groups, hexanamido groups, capryloylmido groups; 1-carboxylmethyl butanylamino groups, 2-bromoacrylamido groups, acrylonitrile groups, ethoxycarbonyl groups, acetyl; acryloyloxyl groups; isopropylsulfinyl, etc. When the acyclic hydrocarbyl groups are interrupted by a functional group described above, the unrestrictive examples are methylene oxy, ethylene oxy, decylene oxy, diglycol moiety, diisopropylene glycol moiety, diethylamine moiety, diethylenetriamine moiety, triethylenetetramine moiety, diethanolamine moiety etc.

The rings in the ring structures described above are for example saturated cyclic hydrocarbons, unsaturated cyclic hydrocarbons, saturated heterocyclic hydrocarbons, and unsaturated heterocyclic hydrocarbons. The rings in the ring structures preferably have 5-6 ring atoms. The ring atoms in the ring structures may comprise one or more hetero atoms selected from O, N, and S. The number of hetero atoms may be determined as required, for example 2-3, preferably 1-2.

The saturated cyclic hydrocarbons include for example cyclohexane, cyclopentane, cyclopentanone, and cyclohexanone. It needs to be indicated that hydrocarbons like cyclopentanone and cyclohexanone are included in the saturated cyclic hydrocarbons. The unsaturated cyclic hydrocarbons include for example benzene, cyclopentene, cyclohexene, and cyclohexadiene. The saturated heterocyclic hydrocarbons include for example oxocyclopentane, oxocyclohexane, piperidine, dioxocyclopentane, dioxocyclohexane, thiocyclopentane, thiocyclohexane, caprolactam, caprolactone, oxocyclopentanone, oxocyclohexanone. The unsaturated heterocyclic hydrocarbons include for example oxocyclohexene, thiocyclohexene, furan ring, pyrrole ring, thiophene ring, pyridine, pyrimidine, imidazole, benzocyclohexanone, benzo-oxocyclohexanone, and oxocyclohexano-benzocyclohexanone. The ring structures may be symmetrically or asymmetrically distributed over the mono-xanthone unit. Knowing from above, these ring structures may be substituted, for example by one or more of the functional groups selected from below: a $C_{1-18}$ acyclic hydrocarbyl groups, preferably a $C_{1-8}$ acyclic hydrocarbyl groups, more preferably a $C_{1-5}$ acyclic hydrocarbyl groups, and particular preferably a $C_{1-3}$ acyclic hydrocarbyl groups, which may be substituted or unsubstituted and/or interrupted by a functional group, and the definitions of the substituents and functional groups are as shown in the description above for "alkyl groups"; halogen atoms, such as chlorine, bromine and iodine; carboxyl groups, sulfonic acid groups, ester groups, nitro groups, acyl halide groups, amine groups, hydroxyl groups, amide groups, aldehyde groups, sulfonic acid groups, thiol groups, ketone groups, sulfonyl groups, and sufinyl groups, where the number of carbon atoms on the backbone is generally no more than 18, preferably no more than 15, particularly preferably no more than 8, and even more preferably no more than 5.

For the sake of simplicity and convenience, shown below are examples of mono-xanthone with the ring structures described above but without any substituent, only.

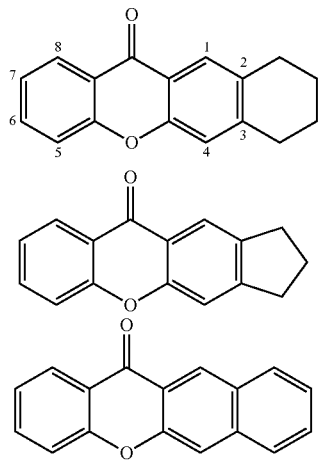

-continued

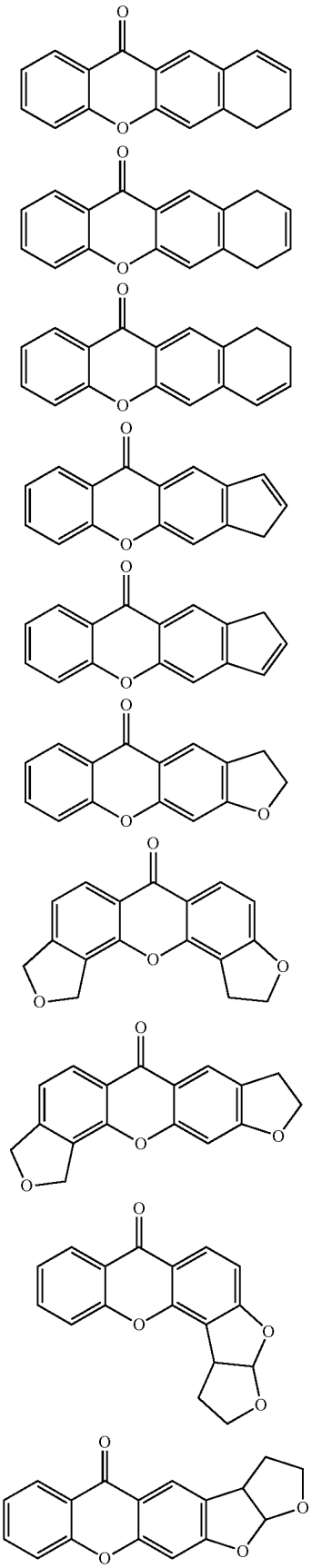

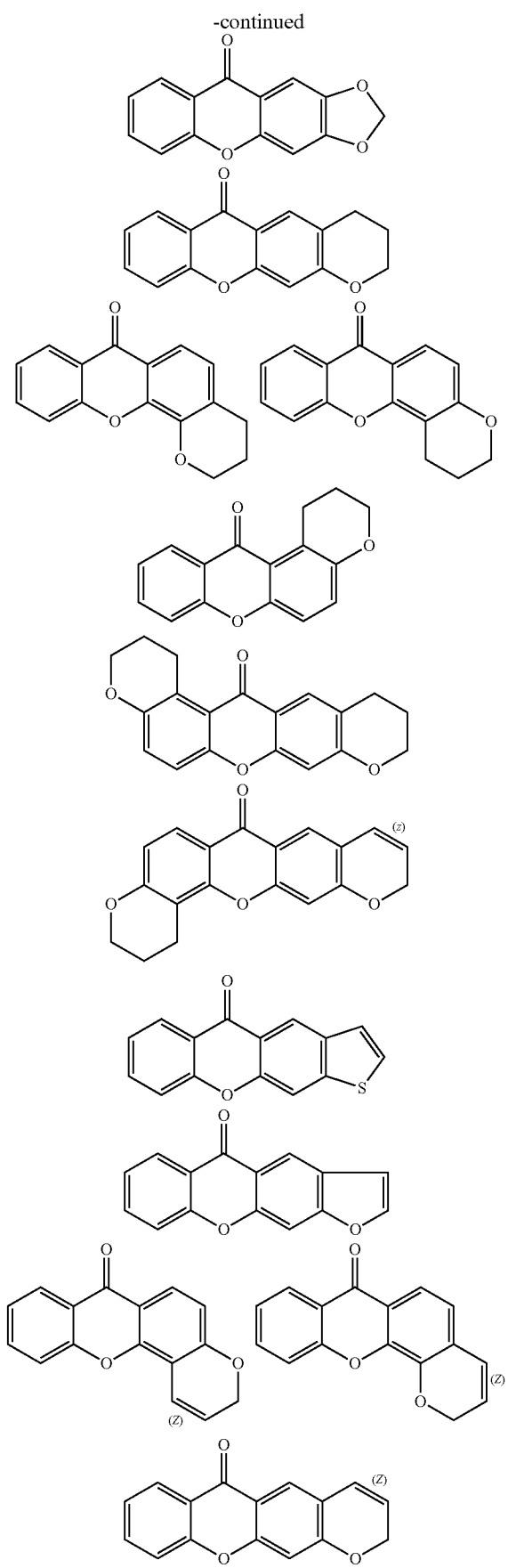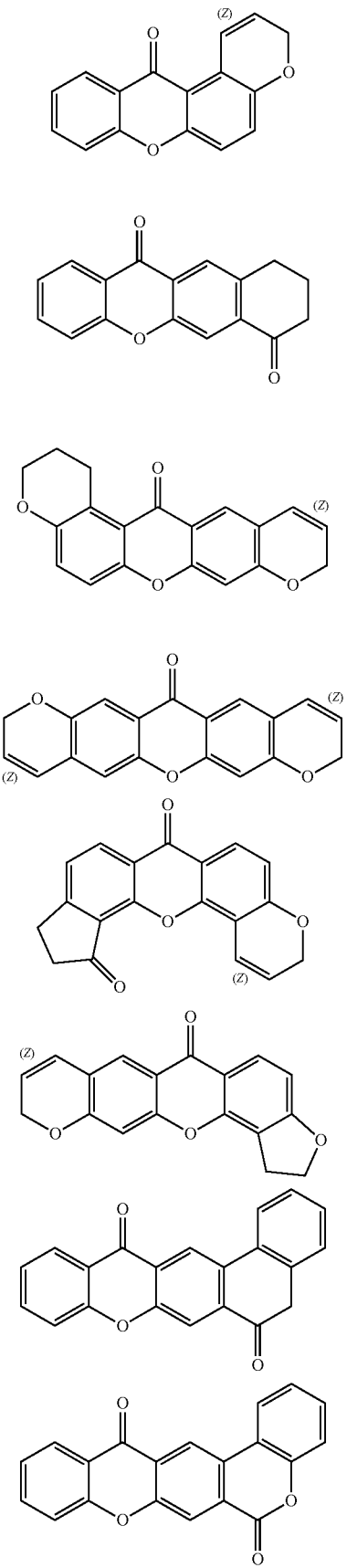

-continued

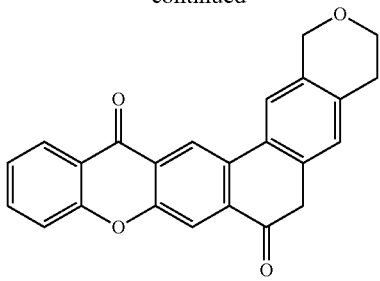

In a most preferred embodiment, the variety, position and size of the substituents mentioned above should meet such requirements as not significantly decreasing the photosensitivity of the group X and having insignificant steric hindrance to the coupling of the modification molecule on the surface of polymer material. In this method, the substituents are preferably at 2 to 7-positions, and the size of substituent at 1-position and 8-position should be comparatively small.

These descriptions on substituents are also applicable for other xanthone structures mentioned above.

The functional group L may be a chemical or biological group. The chemical groups include for example —COOH (carboxyl groups), —COOR' (carboxylic ester groups, including aliphatic hydrocarbyl esters, hydroxyl esters, glycidyl esters thereof, etc.), —COO$^-$M$^+$ (carboxylate groups where M$^+$ represents a monovalent positive ion, e.g. an alkali metal ion such as Li$^+$, Na$^+$, K$^+$, and NH$_4$$^+$), —SO$_3$H (sulfonic acid groups), —SO$_3$R' (sulfonic acid ester groups, including aliphatic hydrocarbyl esters, hydroxy esters, glycidyl esters thereof, etc.), —SO$_3$$^-$M$^+$ (sulfonate groups, wherein M$^+$ represents monovalent positive ions, e.g. alkali metal ions such as Li$^+$, Na$^+$, K$^+$, and NH$_4$$^+$), —COX (acyl halide groups, e.g. acyl chloride, acyl bromide, etc.), —CONHNH$_2$ (acid hydrazide groups), —NHCONHNH$_2$ (semicarbazide groups), —NHCSNHNH$_2$ (thiosemicarbazide groups), —CN (nitrile groups), —CHO (aldehyde groups), —COR' (carbonyl groups, where R' includes methyl, ethyl, propyl, etc.), —OH (hydroxyl groups), —SH (thiol groups), —SSR' (disulfides, where R' includes methyl, ethyl, propyl, etc.), —NH$_2$ (amine groups, including primary amine groups, secondary amine groups, tertiary amine groups, etc.), ammonium salt groups (including —NH$_3$$^+$X$^-$, such as —NH$_3$$^+$Cl$^-$, —NH$_3$$^+$Br$^-$), —NHNH$_2$ (hydrazine groups), —OR' (ether groups, where R' includes methyl, ethyl, propyl, etc.), —SR' (thio-ether groups, where R' includes methyl, ethyl, propyl, etc.), epoxide groups (the number of atoms in a single ring is generally no more than 8, for example no more than 6, or no more than 4, and may include ethylene oxide, propylene oxide, dioxocyclobutane, oxocyclohexane, etc.), —X (halogen atoms, including F, Cl, Br, I, etc.), —NO$_2$ (nitro groups), —R' (hydrocarbyl groups), —R'X$_n$ (halogenated hydrocarbyl groups, where X includes F, Cl, Br, I, etc., n≦(2×the number of carbon atoms in the R'+1)), where R' represents hydrocarbyl groups, such as saturated or unsaturated, branched or unbranched acyclic hydrocarbyl groups in which the number of carbon atoms may be no more than 20 according to the need, preferably no more than 15, more preferably no more than 10, particularly preferably no more than 6, e.g. methyl, ethyl, propyl, tertiary butyl, butenyl etc.; and/or the functional groups L are derived from heterocyclic rings, such as oxygen-containing heterocyclic rings, nitrogen-containing heterocyclic rings, sulfur-containing heterocyclic rings, e.g. pyridine, pyrimidine, piperidine, succinimide, caprolactam, maleimide, furan, thiazole, etc.; metal complexes, e.g. porphyrin complexes, polypyridine complexes, and metal complexes such as ferrocene complexes; onium salts, e.g. pyrilium salts, sulfonium salts, nitronium salts; biological groups such as phosphorylcholines, theophyllines, carbohydrates (including monosaccharides, oligosaccharides, oligomeric polysaccharides, etc.), antibiotics (including penicillin, etc.), vitamins (including vitamin H, etc.), toxins, herbicides, pesticides, steroids, polypeptides, nucleotides, polypeptide nucleic acids, haptens, etc.

The length, flexibility and solubility of the linker should be comprehensively taken into consideration in selecting linker S. Generally, the length of linker S should be no more than 40 nm; in certain instances, length of linker S should be no more than 10 nm. The longer the linker is, the more functional groups it can be linked. The flexibility of the chain determines the mobility of functional groups. Generally speaking, linkers with higher flexibility are favorable to the movement of functional groups; on the contrary linkers with lower flexibility will restrict the movement of functional groups. The solubility of the linker is an important factor that adjusts the solubility of the whole synthesized modification molecule. Generally, the influence of photosensitive and functional groups on the solubility of the modification molecule is determined when both are selected. Thus, in order to obtain modification molecule with solubility in different solvents, linkers with different solubility-related properties should be selected. Generally, linkers with strong water solubility can enhance the water solubility of the modification molecule, while linkers with strong oil solubility can enhance the solubility of the modification molecule in organic solvents.

In a preferred embodiment, comprehensively considering the three aspects above, useful linkers S may be a C$_{1-20}$ hydrocarbyl groups, for example a C$_{1-10}$ hydrocarbyl groups, including saturated or unsaturated hydrocarbyl groups, which may optionally have small number of branches and/or aromatic groups, which is substituted or unsubstituted and/or interrupted by a functional group. The hydrocarbyl groups may be substituted or interrupted by one or more functional groups selected from below: carboxyl groups, hydroxyl groups, amine groups, imine groups, thiol groups, sulfonic acid groups, halogen atoms, ester functional groups, acyl halide groups, acid hydrazide groups, semicarbazide groups, thiosemicarbazide groups, aldehyde groups, ketone groups, epoxide groups, ether groups, thio-ether groups, carbonyl, sulfonyl groups, sulfinyl groups, nitro groups, nitrile groups, phosphoryl functional groups, furan functional groups, carbohydrate functional groups and acyl functional groups. Useful linkers S also include polyethylene glycol, oligo/poly-amides such as poly-β-alanine, polyglycine, polylysine, polypeptides, oligosaccharides, oligo/poly-phosphate esters or phosphate salts such as phosphate mono-ester, phosphate di-ester, phosphate mono-amide, phosphate di-amide, and oligo/poly-sulfamides/sulphonic acid esters, etc. In addition, the linker S may consist of a single kind of above-mentioned unit, or a combination of above-mentioned units.

In this method, the following factors should be taken into consideration in the selection and formulation of the solvent used for mixing with molecule X-S-L or X-L: (1) molecule X-S-L or X-L should be to certain extent soluble in the solvent, and molecule X-S-L or X-L can be present in the solvent in dissolved state or micelle state; (2) the solvent is not reactive towards any functional groups of the molecule X-S-L or X-L, no mater whether the molecule is in ground state or excited state; (3) the solvent does not adversely affect the properties of the functional groups, especially the biological properties; (4) the solvent should be a poor solvent for the modified polymer.

Examples of suitable solvents include organic solvents, e.g. dichloromethane, tetrahydrofuran, ethanol, methanol, acetone, etc; water; mixed solvents formed by water and some organic solvents in a certain proportion; as well as some aqueous solutions of inorganic salt, etc. In mixed solvents of water and some organic solvents, water may count for less than 97% in volume fraction, preferably less than 5%, and the organic solvent may be acetone, ethanol, methanol, etc. When aqueous solutions of inorganic salts are chosen as the solvent, sodium chloride and potassium chloride may be selected as the solute which may be present in less than 3% in mass fraction, preferably less than 0.5%.

In this method, the concentration of the solution obtained by mixing molecule X-S-L or X-L with solvent may range from $10^{-7}$ mM to $10^3$ mM, preferably from $10^{-3}$ mM to 3.0 mM, and most preferably from 0.1 mM to 1.0 mM. The process of mixing with the solvent may be facilitated by the introduction of a buffer solution, an acid or a base, so as to control the pH of the solution within the range of 0-7 or 7-12, according to the requirement based on reaction conditions There is no special limitation on the polymer material to be modified in accordance with the present method, as long as there are a certain amount of active atoms on the surface of the polymer material. Examples of polymer materials suitable for the present method include polyolefins, such as polyethylene, polypropylene, polystyrene, polyvinyl chloride; rubbers, such as styrene butadiene rubber, butadiene-acrylonitrile rubber, SBS, ethylene propylene rubber, chloroprene rubber, silicon rubber, chlorohydrin rubber; polyurethanes; polyamides, such as polycaprolactam; polycarbonates, such as polyhexamethylene carbonate; polyimids; polyesters, such as polyethylene terephthalate, polycaprolactone; fluoro-resins, such as polytetrafluoroethylene, tetrafluoroethylene-hexafluoropropylene copolymer; polyethers, such as polyphenylene oxide, polyethylene glycol; polyvinyl alcohols; polyvinyl acetate; polyacrylates, such as polymethyl methacrylate; biopolymers, such as chitin, chitosan, poly-amino acids, poly-lactic acids; or the blends, composites thereof. The commonly used ones include high density polyethylene, low density polyethylene, cast polypropylene, biaxial oriented polypropylene, butyl rubber, styrene butadiene rubber, natural rubber-styrene butadiene rubber blend, chlorohydrin rubber, polystyrene, tetrafluoroethylene-hexafluoropropylene copolymer, polyimides, polycarbonates, polyethylene terephthalate, etc.

In some cases, the shape of the polymer materials to be modified should meet the following requirements: the surface of the polymer material allows formation of a modification solution layer and may be reached by UV with a certain intensity, e.g. sheets and films. These materials may be solid single polymeric materials, blending materials of polymers, laminates, or organic coating on nonmetal or metallic bases.

Methods well-known to those skilled in the art can be used to evenly cover a layer of modification solution on the surface of the polymer material to be modified: drop casting, impregnation, spin coating, spread coating, and "sandwich"-structure cladding, etc. For example, the spread coating method can be found in Lanmuir 2000, 16, 9331-9337.

The UV illuminant used for irradiation may be a low-pressure, medium-pressure, or high-pressure mercury lamp or other devices that can emit ultraviolet light wave band, and a high-pressure mercury lamp is preferred. The wavelength of UV ranges from 190 to 420 nm, and the intensity of UV may be set within 100.0 mw/cm$^2$, preferably within an intensity of 1.0-20.0 mw/cm$^2$ (intensity of UV with wavelength of 254 nm is taken as a reference standard).

According to factors such as intensity of UV, thermostability and light stability of the materials to be modified, suitable irradiation duration may be generally not more than 300 minutes, preferably within 30 minutes, and most preferably within 2-15 minutes.

In this method, the residue of X-S-L or X-L on the surfaces may be removed by washing. The following factors should be taken into consideration in selecting lotions: (1) the molecule X-S-L or X-L should be to certain extent soluble in the lotion, and the molecules may exist in the lotion in dissolved state or micelle state; (2) the lotion should be a poor solvent for the modified polymer; (3) the lotion is not reactive with any functional group that is introduced onto the modified surface, and does not adversely affect the properties of functional groups, especially the biological properties; (4) the lotion should have a comparatively low boiling point. Examples of suitable agents include water, organic agents such as dichloromethane, tetrahydrofuran, ethanol, methanol, acetone, etc.

In another aspect, the present invention provides a modification compounds used in ultraviolet light-assisted modification method for modifying polymer material surfaces, and the modification compounds have a photosensitive group X and a functional group L, where the photosensitive X comprises at least one xanthone unit.

In an embodiment, the structure of the modification compound may be X-L or X-S-L, where the X is a photosensitive group comprising at least one xanthone unit, the L is a functional group, and the S is a linker. The definition of the photosensitive group X, functional group L, linker S, polymer material P are as described above in the section for "modification method".

In another aspect, the present invention provides the use of the modification compound in the surface modification of polymer materials. The polymer materials are for example polyolefins, rubbers, polyurethanes, polyamides, polycarbonates, polyimides, polyesters, fluoro-resins, polyethers, polyvinyl alcohols, polyvinyl acetates, polyacrylates, biopolymers, or the blends, composites thereof.

Specifically, the polymer material may be polyethylene, polypropylene, polystyrene, polyvinyl chloride, styrene butadiene rubber, butadiene-acrylonitrile rubber, SBS, ethylene-propylene rubber, chloroprene rubber, silicon rubber, chlorohydrin rubber, polycaprolactam, polyhexamethylene carbonate, polyethylene terephthalate, polycaprolactone, polytetrafluoroethylene, tetrafluoroethylene-hexafluoropropylene copolymer, polyphenylene oxide, polyethylene glycol; polyvinyl alcohol, polymethyl methacrylate, chitin, chitosan, poly-amino acids, poly-lactic acids, or the blends, composites thereof.

In addition, the present invention also provides articles having polymer material surfaces formed through modification with the method described above.

The scope of application of the above-mentioned embodiments may include the following aspects:

1. To improve the biological performance of the polymers, where it can be used as the carriers for immunoassay (e.g. pore plate, etc.), carriers for cell culture (e.g. culture tube, culture flask, Petri dish, etc.), carriers for bioassay and bioseparation (e.g. microspheres, microbeads, etc.), and as the carriers for solid phase synthesis.

2. To improve the surface hydrophilicity of polymer materials, where it can be specifically used in: (1) preparation of novel PE greenhouse film preventing formation of water drops; (2) enhancing the dyeability of fibers; (3) preparation of antistatic fabrics; (4) improving the dyeability of bumpers.

3. To improve the oxygen and water resistance capacity of polymer surfaces, where for example, it can be used in preparing new packing materials.

4. To improve the cohesiveness of polymer surfaces, where for example, it can be used in preparing laminated packing materials, and can also be used to enhance the cohesiveness between polymer materials and other metal or nonmetal materials.

This method has the following advantages: (1) good modification effect, simple operation, fast, low cost, low environmental pollution; (2) wide scope of suitable functional groups, and the structure of functional groups are not vulnerable for attack during the operation; (3) groups with different properties can be introduced simultaneously onto a surface.

EMBODIMENT

Figure 1:
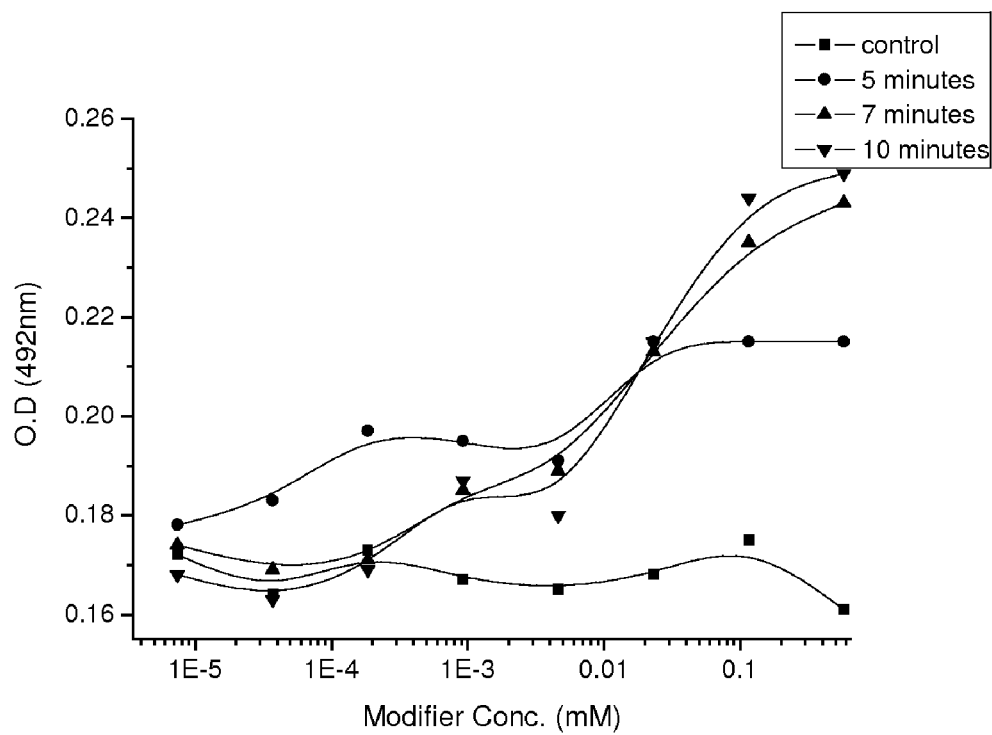
FIG. 1. Influence on the modification effect of PS surface by changing the concentration of compound 6 and irradiation duration FIG. 2. Effect of compound 2, 4, 6 on the modification of PS surface FIG. 3. Schematic view of "sandwich"-structure reactor FIG. 4. Influence of the concentration of compound 7 on the modification effect of BOPP film surface FIG. 5. Influence of UV irradiation duration on the modification effect of BOPP film surface

The present invention will be demonstrated by, but by no means limited to the following embodiments.

Abbreviation of commonly used compounds and special terms involved in the embodiments:

2-XTC: xanthone-2-carboxylic acid
Boc: tert-butoxycarbonyl
DMF: N,N'-dimethyl formamide
CDI: N,N'-carbonyldiimidazole
TEA: triethylamine
DIEA: diisopropylethylamine
BOP: BOP Reagent
Boc-β-Ala-OH: tert-butoxycarbonyl-β-alanine
DMSO: dimethyl sulfoxide
OPD: o-phenylendiamine dihydrochloride
PEG300: polyethylene glycol (average molecule weight: 300)
Ph₃CCl: triphenylchloromethane
PEG300-CPh₃: polyethylene glycol (300)-triphenylmethyl ether
PS: polystyrene
BOPP: biaxial oriented polypropylene
LDPE: low-density polyethylene
F46: tetrafluoroethylene-hexafluoropropylene copolymer
IIR: butyl rubber
SBR: styrene butadiene rubber
CHR: chloro hydrin rubber
NR/SBR: natural rubber-styrene butadiene rubber blend
PC: polycarbonate
PI: polyimide
PET: polyethylene terephthalate
¹H NMR: ¹H nuclear magnetic resonance Example 1

Synthesis of Molecule X-S-L or X-L

Synthesis of tert-butyl N[3-(xanthone-2-formamido)propyl]-carbamate (compound 1)

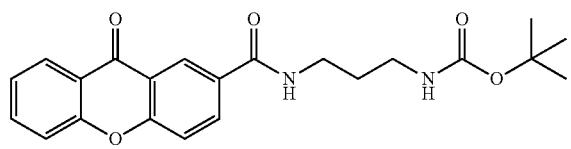

Dissolving 2-XTC (13.2 g, 55 mmol) into DMF (120 ml), stiffing to promote the dissolution in a 40° C. water bath. Adding CDI (9.25 g, 57 mmol) once into the solution, carrying out reaction with stiffing for 4 hours and 40 minutes. Transferring the reaction system out, cooling with stiffing in a 20° C. water bath for 10 minutes. Dissolving mono-substituted tert-butoxycarbonyl-1,3-propylene diamine (11.09 g, 67 mmol) into TEA/DMF solution (20 ml, 10% v/v), mixing well, which is then added once into the reaction system of xanthone-2-carboxylic acid with CDI, and then adding TEA (13 ml), warming up to 40° C. with stiffing, reacting for 11 hour. Cooling the reaction system to 0° C., adding deionized water (700 ml), precipitating, vacuum filtrating, drying the solid obtained in an approximately −0.09 MPa vacuum condition at 40° C. Yield: 41.47% (based on 2-XTC).

¹H NMR (600 MHz, DMSO-d₆): δ 8.76 (1H), 8.72 (1H), 8.32 (1H), 8.24 (1 H), 7.93 (1H), 7.76 (1H), 7.71 (1H), 7.52 (1H), 6.79 (1H), 3.31 (2H), 3.00 (2H), 1.67 (2H), 1.38 (9H) ppm.

Synthesis of 3-(xanthone-2-formamido)propyl ammonium chloride (compound 2)

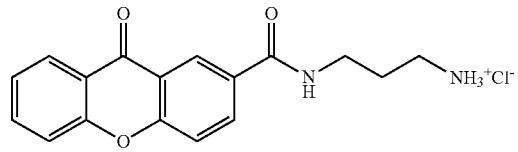

Putting compound 1 (4.06 g, 10.25 mmol) into methanol (120 ml) and stiffing to make it dispersed, adding hydrochloric acid/methanol solution (5.4 M, 20 ml) after stiffing for 20 minutes. Warming up with stirring in a 73° C. water bath until reflux occurs, keeping reacting for 2.5 hours. Placing the reaction system in a freezing chamber; adding anhydrous ether (300 ml), precipitating, vacuum filtrating, washing the solid obtained with anhydrous ether (150 ml), and then drying in an approximately −0.09 MPa vacuum condition at 40° C. Yield: 88.02% (based on compound 1).

¹H NMR (600 MHz, DMSO-d₆): δ 8.99 (1H), 8.74 (1H), 8.36 (1H), 8.24 (1 H), 7.96-7.85 (3H), 7.94 (1H), 7.78 (1H), 7.72 (1H), 7.53 (1H), 3.40 (2H), 2.86 (2H), 1.86 (2H) ppm.

Synthesis of tert-butyl N-[3-(xanthone-2-formamido)-propyl]-carbamoylethyl-carbamate (compound 3)

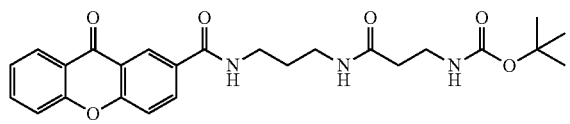

Dissolving BOP (1.90 g, 4.3 mmol) and Boc-β-Ala-OH (0.89 g, 4.7 mmol) into TEA/DMF (29 ml, 10% v/v), stiffing at 20° C. for 10 minutes. Adding once compound 2 (1.27 g, 4.3 mmol), reacting at 19° C.-20° C. with stirring overnight. Adding deionized water (350 ml) to precipitate, vacuum filtrating, drying the solid obtained in an approximately −0.085 MPa vacuum condition at 40° C. Yield: 77.86% (based on compound 2).

¹H NMR (600 MHz, DMSO-d₆): δ 8.76 (1H), 8.72 (1H), 8.32 (1H), 8.24 (1 H), 7.92 (1H), 7.85 (1H), 7.77 (1H), 7.72 (1H), 7.52 (1H), 6.70 (1H), 3.32 (2H), 3.31 (4H), 2.23 (2H), 1.69 (2H), 1.37 (9H) ppm.

Synthesis of 3-(xanthone-2-formamido)propyl-carbamoylethyl ammonium chloride (compound 4)

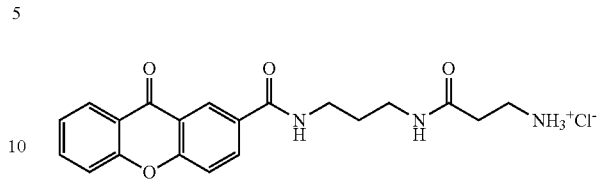

Dissolving compound 3 (1.52 g, 3.25 mmol) into methanol (70 ml), adding hydrochloric acid/methanol (5 ml, 5.4 M HCl), warming up with stiffing in a 73° C. water bath until reflux occurs, keeping reacting for 2.5 hours. Decompressing to remove large amount of solvent, adding ether (100 ml) into the residue, vacuum filtrating, washing the solid obtained with ether (150 ml), and then drying in an approximately −0.09 MPa vacuum condition at 40° C. Yield: 83.29% (based on compound 3).

¹H NMR (600 MHz, DMSO-d₆): δ 8.82 (1H), 8.72 (1H), 8.33 (1H), 8.24 (1 H), 8.13 (1H), 7.94 (1H), 7.90-7.60 (3H), 7.78 (1H), 7.72 (1H), 7.53 (1H), 3.34 (2 H), 3.17 (2H), 3.00 (2H), 2.47 (2H), 1.72 (2H) ppm.

Synthesis of tert-butyl N—{N-[3-(xanthone-2-formamido)-propyl]-carbamoylethyl}-carbamoylethyl-carbamate (compound 5)

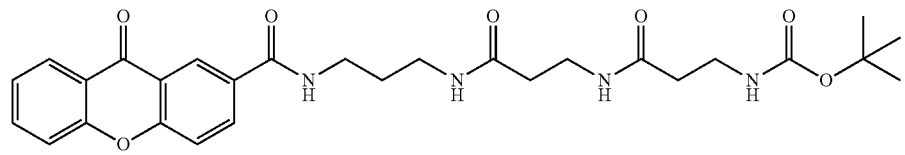

Dissolving BOP (2.86 g, 4.54 mmol) and Boc-β-Ala-OH (0.98 g, 5.0 mmol) into TEA/DMF (53 ml, 10% v/v), stirring at 20° C. for 10 minutes; adding once compound 4 (1.83 g, 4.54 mmol), then adding TEA/DMF (47 ml, 10% v/v), carrying out reaction overnight with stiffing. Adding deionized water (3000 ml), precipitating, vacuum filtrating, washing the solid obtained with deionized water, and then drying it in an approximately −0.09 MPa vacuum condition at 75° C. Yield: 74.08% (based on compound 4).

$^1$H NMR (600 MHz, DMSO-$d_6$): δ 8.78 (1H), 8.72 (1H), 8.32 (1H), 8.23 (1 H), 7.92 (1H), 7.87 (1H), 7.86 (1H), 7.77 (1H), 7.72 (1H), 7.52 (1H), 6.67 (1H), 3.36 (2H), 3.24 (2H), 3.14 (2H), 3.09 (2H), 2.24 (2H), 2.20 (2H), 1.69 (2H), 1.36 (9H) ppm.

Synthesis of N—{N-[3-(xanthone-2-formamido)-propyl]-carbamoylethyl}-carbamoylethyl-ammonium chloride (compound 6)

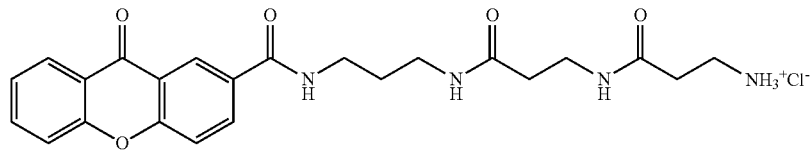

Dissolving compound 5 (2.10 g, 3.90 mmol) into methanol (150 ml), adding HCl/methanol solution (11 ml, 5.4 M HCl), warming up in a 73° C. water bath with stiffing until reflux occurs, keeping reacting for 2.5 hours. Decompressing to remove the solvent and obtain the product. Yield: 31.22% (based on compound 5).

$^1$H NMR (600 MHz, DMSO-$d_6$): δ 8.82 (1H), 8.72 (1H), 8.34 (1H), 8.24 (1 H), 8.14 (1H), 7.99 (1H), 7.94 (1H), 7.81 (3H), 7.77 (1H), 7.72 (1H), 7.53 (1H), 3.33 (2H), 3.29 (2H), 3.14 (2H) 2.98 (2H), 2.27 (2H), 2.45 (2H), 1.70 (2H) ppm.

Synthesis of 3{N-[3-(xanthone-2-formamido)-propyl]-carbamoyl}-propanoic acid (compound 7)

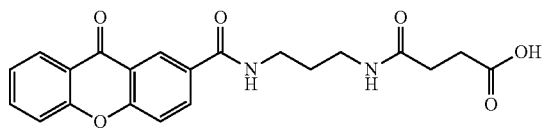

In a 20° C. water bath, adding compound 2 (0.50 g, 1.5 mmol) into DMF (40 ml) and stirring for 10 minutes to make it dispersed, and then adding butanedioic anhydride (0.30 g, 3.0 mmol), then adding triethylamine (2.0 ml). Carrying out reaction for 3 hours, adding HCl (25 ml, 1.0M) and deionized water (315 ml) into the reaction system, stirring in ice water bath for 4 hours, precipitating to obtain a white solid; vacuum filtrating, washing the solid with deionized water (300 ml), and drying it in an approximately −0.09 MPa vacuum condition at 40° C. Yield: 87.54% (based on compound 2).

$^1$H NMR (600 MHz, DMSO-$d_6$): δ 12.04 (1H), 8.77 (1H), 8.72 (1H), 8.32 (1 H), 8.24 (1H), 7.92 (1H), 7.77 (1H), 7.72 (1H), 7.52 (1H), 3.32 (2H), 3.13 (2H), 2.43 (2H), 2.32 (2H), 1.68 (1H) ppm.

Synthesis of N-[3-(xanthone-2-formamido)-propyl]-thiosemicarbazide (compound 8)

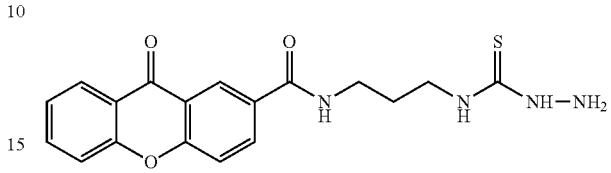

Dissolving BOP (0.44 g, 1.0 mmol) in DMF (20 ml), adding in turn $CS_2$ (0.6 ml, 10.0 mmol), compound 2 (0.35 g, 1.0 mmol) and TEA (0.42 ml, 3.0 mmol), carrying out reaction with stirring in a 20° C. water bath for 1.5 hours. Removing the remaining $CS_2$ in vacuum condition. In a ice water bath, dropping the above reaction solution in DMF solution (5.0 ml) of hydrazine hydrate (0.8 ml, 14.0 mmol); And then stirring in a 20° C. water bath and keeping reacting overnight. Adding deionized water (100 ml), precipitating, vacuum filtrating, washing the solid with deionized water (200 ml), and then drying it in an approximately −0.09 MPa vacuum condition at 40° C. Yield: 67.43% (based on compound 2).

$^1$H NMR (600 MHz, DMSO-$d_6$): δ 8.85 (1H), 8.72 (1H), 8.61 (1H), 8.32 (1 H), 8.23 (1H), 8.04 (1H), 7.91 (1H), 7.77 (1H), 7.71 (1H), 7.51 (1H), 4.47 (2H), 3.54 (2H), 3.33 (2H), 1.76 (2H) ppm.

2-chloroformyl-xanthone (compound 9)

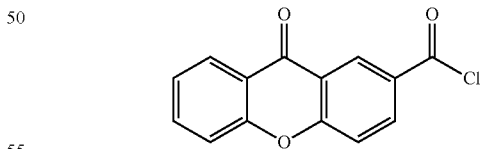

Dispersing 2-XTC (2.41 g, 10.0 mmol) into $SOCl_2$ (50 ml), carrying out reaction with stirring in reflux condition for 4 hours. Decompressing the obtained yellowish brown solution to remove the remaining $SOCl_2$, so as to obtain a yellowish brown solid. Washing the solid with petroleum ether (100 ml) in twice, and then decompressing to remove the petroleum ether. Drying in an approximately −0.09 MPa vacuum condition at 40° C. Yield: 47.12% (based on 2-XTC).

$^1$H NMR (600 MHz, DMSO-$d_6$): δ 9.15 (1H), 8.39 (1H), 8.36 (1H), 7.79 (1 H), 7.61 (1H), 7.55 (1H), 7.46 (1H) ppm.

FITR: ν 1759.68 cm⁻ (C=O), 1671.99 cm$^{-1}$ (C=O), 1606.69 cm$^{-1}$ (C=C), 1315.17 cm$^{-1}$ (C—O—C), 757.88 cm$^{-1}$ (C—H).

Synthesis of 6-(xanthone-2-formamido)-hexanoic acid methyl ester (compound 10)

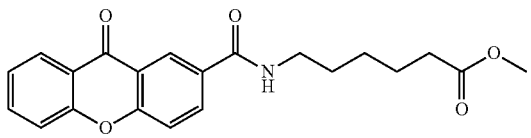

Dissolving 2-XTC (4.80 g, 20.0 mmol) in DMF (130 ml), stirring to promote the dissolution in a 40° C. water bath. Adding once CDI (3.73 g, 23.0 mmol) into the solution, carrying out reaction with stirring for 4 hours. Transferring the reaction system out, stirring it in a 20° C. water bath for 10 minutes and cooling. Adding 6-aminohexanoic acid methyl-ester.HCl (4.55 g, 25.0 mmol) into the reaction system, and then adding TEA (7.0 ml), stirring in a 40° C. water bath and keeping reacting overnight. In an ice water bath, adding deionized water (250 ml) to precipitate, vacuum filtrating, drying the obtained solid in atmospheric pressure at 70° C. Yield: 60.48% (based on 2-XTC).

$^1$H NMR (600 MHz, DMSO-d$_6$): δ 8.78 (1H), 8.71 (1H), 8.31 (1H), 8.23 (1 H), 7.91 (1H), 7.76 (1H), 7.71 (1H), 7.51 (1H), 3.56 (3H), 3.28 (2H), 2.31 (2H), 1.56 (4H), 1.32 (2H) ppm.

Synthesis of 6-(xanthone-2-formamido)-hexanoic acid (compound 11)

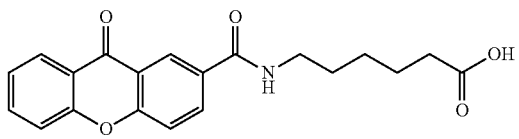

In a 80° C. water bath, stirring compound 10 (3.95 g, 10.7 mmol) in THF (120 ml) to make it dispersed evenly. Preparing 0.5M solution of LiOH (1.35 g, 32.2 mmol), adding once into the above system, stirring for 1.5 hours. Decompressing to remove the THF in the system, and then adding HCl (10.0 ml, 10.0 M), stirring, acidifying and precipitating for 1 hour. Vacuum filtrating, washing the solid with deionized water (350 ml), drying it in an approximately −0.09 MPa vacuum condition at 40° C. Yield: 96.78% (based on compound 10).

$^1$H NMR (600 MHz, DMSO-d$_6$): δ 11.96 (1H), 8.78 (1H), 8.72 (1H), 8.32 (1 H), 8.24 (1H), 7.92 (1H), 7.76 (1H), 7.52 (1H), 3.28 (2H), 2.22 (2H), 1.56 (4H), 1.34 (2H) ppm.

Synthesis of 6-(xanthone-2-formamido)-hexanoic acid hydrazide (compound 12)

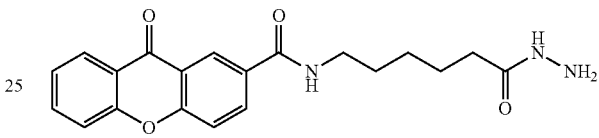

Dispersing compound 10 (0.37 g, 1.0 mmol) into methanol (20 ml), adding once hydrazine hydrate (1.2 ml, 21.0 mmol), keeping reacting for 6 hours in reflux condition. Cooling to room temperature, decompressing to remove the solvent; once again dispersing the residue into ice water (20 ml), vacuum filtrating, washing the solid with water, drying it in an approximately −0.09 MPa vacuum condition at 40° C. Yield: 34.33% (based on compound 10).

$^1$H NMR (600 MHz, DMSO-d$_6$): δ 8.95 (1H), 8.77 (1H), 8.72 (1H), 8.32 (1 H), 8.24 (1H), 7.92 (1H), 7.76 (1H), 7.72 (1H), 7.52 (1H), 4.39 (2H), 3.28 (2H), 2.03 (2H), 1.60-1.51 (4H), 1.30 (2H) ppm.

Synthesis of N-[3-(xanthone-2-formamido)-propyl] N-[(4-O-(α-D-glucopyranosidyl)-β-D-glucopyranosidyl)]N-acetyl ammonia (compound 13)

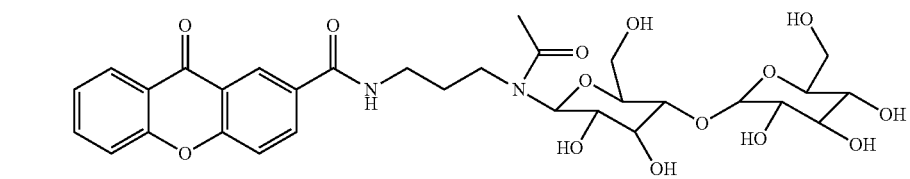

Dissolving compound 2 (0.50 g, 1.5 mmol) and maltose (1.54 g, 4.5 mmol) in anhydrous methanol (80 ml). Adding DIEA (0.35 ml, 2.0 mmol), carrying out reaction with stiffing overnight in 60° C. water bath and nitrogen atmosphere. And then placing the system in ice bath to cool with stirring, adding acetic anhydride (3.5 ml). Standing overnight with stiffing at room temperature. Decompressing to remove the solvent, dissolving the residue in water, filtrating, and freeze drying; separating the solid obtained with column chromatography, using silica gel (100-200 mesh) as immobile phase, water as eluent to separate the remaining maltose, and acetonitrile/water (v/v=50/50) as eluent to separate compound 13 to obtain the target product by freeze drying. Yield: 53.26% (comparative to compound 2).

$^1$H NMR (600 MHz, DMSO-d$_6$): δ 8.76 (1H), 8.72 (1H), 8.32 (1H), 8.24 (1 H), 7.93 (1H), 7.77 (1H), 7.72 (1H), 7.52 (1H), 6.79 (1H), 5.79 (1H), 5.04 (1H), 4.43-4.42 (7H), 4.03 (1H), 4.00 (1H), 3.77 (1H), 3.74 (2H), 3.49 (1H), 3.40 (1H), 3.31 (2H), 3.02 (1H), 3.00 (2H), 2.02 (3H), 1.67 (2H) ppm.

Synthesis of xanthone-2-formamido-propylamino-6-ketoestradiol-6-(O-carboxymethyl)-oxime (compound 14)

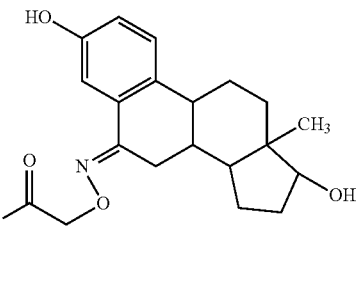

Dissolving compound 2 (0.50 g, 1.5 mmol) and BOP (0.95 g, 1.5 mmol) in DMF (50 ml), adding 6-ketoestradiol-6-(O-carboxymethyl)-oxime (0.54 g, 1.5 mmol) and DIEA (0.53 mL, 3.0 mmol). Carrying out reaction with stirring for 4 hours in a 20° C. water bath, and then adding deionized water (10 ml), vacuum filtrating, washing the solid with Na$_2$CO$_3$ water solution (3×10 ml, 10% wt), 10% KHSO$_4$ water solution (3×10 ml, 10% wt) and deionized water (3×10 ml) in turn, drying it in an approximately −0.09 MPa vacuum condition at 40° C. Yield: 85.26% (based on compound 2).

$^1$H NMR (600 MHz, DMSO-d$_6$): δ 8.82 (1H), 8.72 (1H), 8.33 (1H), 8.24 (1 H), 8.13 (1H), 7.94 (1H), 7.78 (1H), 7.72 (1H), 7.53 (1H), 7.21 (1H), 7.14 (1H), 6.78 (1H), 4.42 (2H), 3.31-1.16 (22H), 0.64 (3H) ppm.

Xanthone 2-carboxylic acid polyglycol ester (compound 15)

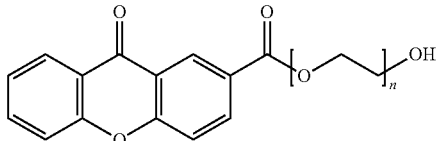

n = 6

Dissolving PEG300 (3.0 g, 10.0 mmol) in pyridine (20 ml), distilling to remove approximately ⅓ of pyridine (azeotropic drying). Dissolving Ph$_3$CCl (0.28 g, 1.0 mmol) in pyridine (6 ml), which is then dropped into the PEG300 solution for no less than 3 hours. Continuing to react with stirring for 18 hours at room temperature. Vacuum distilling to remove the solvent; subsequently, adding toluene (2×25 ml) into the system and distilling. Dissolving the remaining liquid in methylene chloride (100 ml), adding in turn 0.1M of citric acid, saturated sodium bicarbonate, saturated NaCl water solution to wash. Vacuum concentrating the organic phase and column separating the concentrate: silica gel (100-200 mesh) as immobile phase, ethyl acetate/petroleum ether (v:v=50:50) ~ethyl acetate (100%) as mobile phase. The obtained product is a colorless oily liquid. Yield: 85.31%.

$^1$H NMR (600 MHz, CDCl$_3$): δ 7.48 (5H), 7.28 (5H), 7.20 (5H), 3.65 (20 H), 3.58 (2H), 3.25 (2H), 2.95 (1H) ppm.

Dissolving PEG300-CPh$_3$ (0.4 g, 0.74 mmol) and compound 9 (0.19 g, 0.74 mmol) in pyridine (15 ml), carrying out reaction with stirring for 16 hours, distilling to remove the pyridine, and then adding toluene (2×25 ml) and distilling. Dissolving the remaining liquid into methylene chloride (50 ml), adding in turn 0.1M of citric acid, saturated sodium bicarbonate, saturated NaCl water solution to wash. Vacuum concentrating the organic phase and column separating the concentrate: silica gel (100-200 mesh) as immobile phase, ethyl acetate/petroleum ether (v:v=90:10) as mobile phase.

The obtained intermediate product is a yellow oily liquid. Yield: 72.46% (0.41 g). Dissolving the intermediate product in methylene chloride/methanol (10 ml v:v=80:20) mixed solvent, adding $ZnBr_2$ (0.5 g, 2.18 mmol), carrying out reaction with stirring for 20 minutes, evaporating to remove the solvent. Column separating the concentrate: silica gel (100-200 mesh) as immobile phase, ethyl acetate/petroleum ether (v:v=80:20) as mobile phase. The obtained intermediate product is a yellow oily liquid. Yield: 85%.

$^1$H NMR (600 MHz, DMSO-$d_6$): δ 8.74 (1H), 8.23 (1H), 8.26 (1H), 7.93 (1 H), 7.78 (1H), 7.72 (1H), 7.53 (1H), 3.63 (20H), 3.56 (2H), 3.24 (2H), 2.97 (1H) ppm.

Example 2

Dissolving compound 2, 4, 6, 7 into pure water (conductivity=0.8 μs/cm) to prepare 0.05 mM solution. Dissolving 2-XTC, benzophenone into anhydrous ethanol to prepare a 0.064 mM solution and a 0.053 mM solution respectively. Using UV-vis Spectrograph (GBC Cintra20, Australia) to measure the UV spectra of the six solutions described above in a wavelength range of 190-400 nm. Table 1 shows the characteristic absorption wavelength ($\lambda_{max}$) and molar absorption coefficient of light (ε) of the six compounds.

TABLE 1

| | compound 2 | compound 4 | compound 6 | compound 7 | 2-XTC | BP |
|---|---|---|---|---|---|---|
| $\lambda_{max}$ (nm) | 201.5 | 202.3 | — | 194.8 | — | — |
| ε (L·$mol^{-1}$·$cm^{-1}$) | 20000 | 25017 | — | 40427 | — | — |
| $\lambda_{max}$ (nm) | 219.4 | 217.7 | — | — | 220.7 | 216.1 |
| ε (L·$mol^{-1}$·$cm^{-1}$) | 15690 | 17759 | — | — | 7804 | 21937 |
| $\lambda_{max}$ (nm) | 260.4 | 260.4 | 248.8 | 248.6 | 256.6 | 261.8 |
| ε (L·$mol^{-1}$·$cm^{-1}$) | 44259 | 45672 | 43882 | 44630 | 25158 | 19390 |
| $\lambda_{max}$ (nm) | 353.0 | 353.4 | 341.6 | 342.5 | 345.0 | — |
| ε (L·$mol^{-1}$·$cm^{-1}$) | 4983 | 5224 | 4869 | 5264 | 2940 | — |

Example 3

Dissolving compound 6 in distilled water to prepare a solution with the initial concentration at 0.58 mM, and five-fold dilute to prepare a series of modification solution based on the above concentration. Before use, each concentration of solution is passed with nitrogen gas to remove oxygen. Washing a surface-unmodified polystyrene (PS) 96 well plate with anhydrous ethanol and deionized water three times respectively, drying it at 50° C. for 45 minutes for future use. Adding the modification solution above into each well of the plate in an amount of 100 μL/well, placing the plate under a 1000 W high-pressure mercury lamp for irradiation with the light intensity at 3.55 mW/$cm^2$ (λ=254 nm) and duration at 5, 7 and 10 minutes respectively. After irradiation, pouring the modification solution out, washing the plate with deionized water three times, and then drying it at 50° C. for 45 minutes, protect from light for future use. Adding 3.94 μg/mL biotin-OSu ester solution (pH=7.2 phosphate buffer (PBS) as solvent) into each well of the modified plate (100 μL/well), and placing it in an oven at 21-23° C. for incubation overnight; washing three times with Covabuffer, with the last time keeping Covabuffer in well for 10 minutes; Adding a mixed solution of avidin and HRP-avidin (pH=7.2 PBS as solvent, containing 4 μg/mL of avidin, and 0.13 μg/mL of HRP-avidin), 100 μL/well, incubate in an oven at 21-23° C. for 2 hours; washing the plate twice with Covabuffer, with the last time keeping Covabuffer in plate for 10 minutes; pouring the lotion out, adding 100 μL/well of citrate buffer (pH=5.0, containing 0.015% (v/v) $H_2O_2$ and 0.6 mg/mL of OPD) for chromogenic reaction, adding 2.0 N of sulfuric acid 6 minutes later to terminate the reaction; Measuring the absorption of each modified well at 492 nm on a ELISA reader (Multiskan MK3, Thermo). The results are shown in FIG. 1. At low concentration, the irradiation duration does not exert significant influence on surface modification effect; when the concentration of modification solution is lager than $4.64 \times 10^{-3}$ mM, the surface modification effect of PS becomes better as the irradiation duration increases, and the best modification effect is obtained at irradiation of 10 minutes.

Example 4

Figure 2:
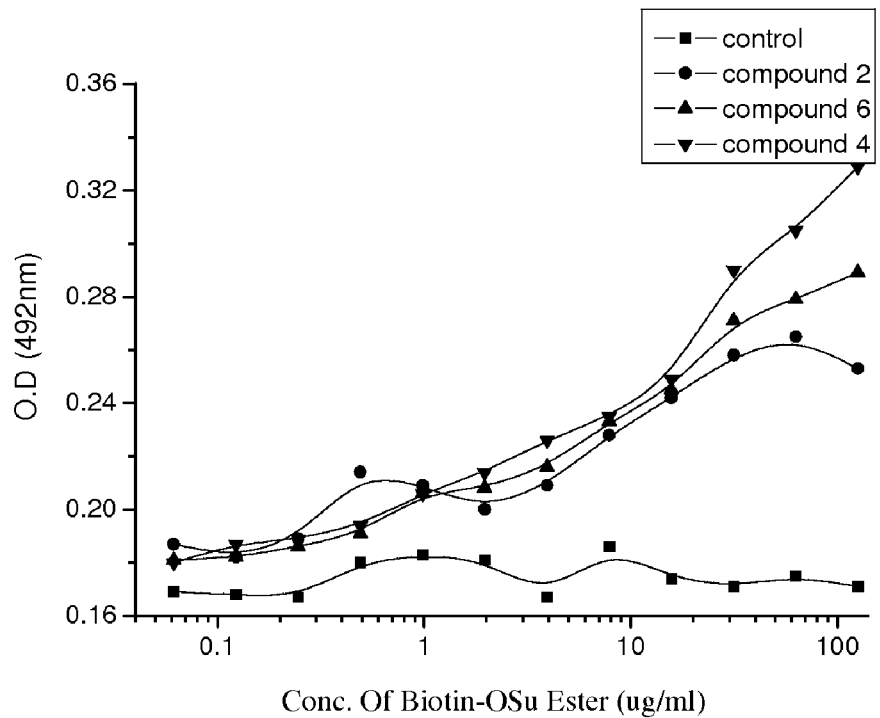

Dissolving compounds 2, 4, and 6 in distilled water to prepare 0.1 mM modification solutions. The oxygen removal operation of modification solution and pre-treatment of surface-unmodified PS 96 well plate are the same as those of example 3. Adding the above three modification solutions into each well of the plate (100 μL/well), and the irradiation and post-treatment are also the same as those of example 3. Preparing a biotin-OSu ester (pH=7.2 PBS as solvent) solution with concentration of 126 μg/mL, two-fold dilute to obtain a series of solutions, adding each concentration of solution into the compound 2, 4, 6 modified well respectively, and the subsequent wash, avidin adsorption, chromogenic reaction and absorption measurement are also the same as those of example 3. The results are shown in FIG. 2. It is found that compound 4 has the best modification effect on PS well plate, and compound 6 and compound 2 exhibit comparatively poorer modification effect.

Example 5

Preparing a 0.1 mM modification solution of compound 4 by using the same formulation method and oxygen removal operation as those of example 3. Taking five PS96 well plates, which is pre-treated the same as example 3. Adding compound 4-modification solution respectively, and carrying out surface modification according to the method of example 3. Subsequently, adding 126 μg/mL biotin-OSu ester solution (pH=7.2 PBS as solvent) into modified well, and the subsequent wash, avidin adsorption, chromogenic reaction and absorption measurement are also the same as those of example 3. The results are shown in table 2. It is found that it is well repeatable to carry out surface modification on different PS96 well plates.

TABLE 2

Repeatability of PS surface modification with compound 4

| Average absorption(492 nm) | Deviation | Deviation percentage % |
|---|---|---|
| 0.324 | 0.011 | 3.4 |

Example 6

Dissolving compound 6 in pure water (conductivity=0.8 μs/cm) to prepare a 1.0 mmol/L modification solution.

Figure 3:
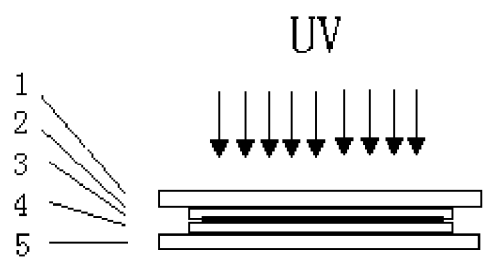

FIG. 3 is an schematic view of the "sandwich"-structure reactor used in this example, and the characteristic function of components are as follows: component 1 is an upper quartz plate, through which ultraviolet light irradiate downwards to initiate the photochemical reaction between components 2, 3, and 4, besides the component 1 also provides a certain pressure on the component 2, 3 and 4, which makes them combine with each other more compactly; component 2 is an upper substrate that has to have enough penetrability for ultraviolet light, it should not absorb the ultraviolet light at the characteristic wavelength needed for UV assisted surface modification, and also it per se can be the modified polymer material; component 3 is a modification solution, which modifies component 2 and 4 through the inducement of UV light; component 4 is a lower substrate, which is the modified polymer material; component 5 is a lower quartz plate, which bears the weight of the four components above. According to actual demands, any of the components 1, 2 or 5 may be discarded. In this example, the integrated "sandwich"-structure reactor consisting of the five components described above is selected.

Taking BOPP film and PS plate as the upper and lower substrates and the modification solution described above to prepare a "sandwich"-structure reactor as shown in FIG. 3. At room temperature, placing the "sandwich"-structure reactor under a 1000 W high-pressure mercury lamp (light intensity of 7.0 mw/cm$^2$ at λ=254 nm) for irradiations, which last for 0.5, 2.0, 5.0 and 10.0 minutes respectively. Washing the treated PS plate and BOPP film with large amount of water firstly and then with anhydrous ethanol, so as to remove the moisture attached on the surface of the substrates, putting in air for more than 15 minutes to allow complete volatilization of the anhydrous ethanol.

Measuring the modified PS plate and BOPP film for air/water contact angle (CA), which is an index used to characterize the hydrophilicity of polymer surfaces, the smaller CA the better hydrophilicity. Method: at room temperature, dropping perpendicularly 1 μl of deionized water onto the surface each time, and immediately recording the CA with an OCA20 contact angle analyzer produced by Dataphysics instruments, Germany. At least 6 points are measured for each sample (the same below). The results are shown in table 3.

TABLE 3

Changes of water contact angle of compound 6 modified PS plate and BOPP film

| | | Irradiation duration (minute) | | | | Water CA before modification |
|---|---|---|---|---|---|---|
| | | 0.5 | 2.0 | 5.0 | 10.0 | |
| Water CA after modification | PS | 82.0° | 71.3° | 60.9° | 41.2° | 92.9° |
| | BOPP | 92.7° | 82.9° | 67.5° | 39.8° | 102.2° |

Example 7

Preparing a 0.58 mM modification solution of compound 6 and carrying out oxygen removal treatment according to the method of example 3. Making a "sandwich"-structure reactor by using the method of example 6, using BOPP film as upper substrate, and LDPE film, F46 film, IIR sheet, SBR sheet, CHR sheet, NR/SBR sheet as lower substrates. At room temperature, placing the "sandwich"-structure reactor under a 1000 w high-pressure mercury lamp (light intensity at λ=254 nm: 3.55 mw/cm$^2$) to receive irradiation for 10.0 minutes. Washing the modified substrates such as LDPE film, F46 film, IIR sheet, SBR sheet, CHR sheet, NR/SBR sheet with large amount of water first and then with anhydrous ethanol to remove the moisture attached on the surface of substrates, drying them in a 21-23° C. oven for more than 10 minutes to have the anhydrous ethanol completely evaporated.

The measurement of air/water contact angle of the substrates such as LDPE film, F46 film, IIR sheet, SBR sheet, CHR sheet, NR/SBR sheet before and after modification is the same as that of example 6. The results are shown in table 4. It is found that the compound 6 has good modification effect on surfaces of different substrates based on the comparison of CA before and after modification.

TABLE 4

Comparison of CA of different substrates before and after modification with compound 6

| | F46 | LDPE | IIR | SBR | CHR | NR/SBR |
|---|---|---|---|---|---|---|
| Before modification | 114.2° | 104.0° | 108.5° | 109.7° | 115.6° | 116.8° |
| After modification | 69.6° | 70.7° | 65.8° | 84.7° | 94.3° | 82.6° |

Example 8

Preparing a 2.0 mM modification solution of compound 4 by choosing deionized water, sodium chloride water solution (0.02% wt), water/ethanol (v:v=50:50) mixture as solvent. Making a "sandwich"-structure reactor by using the method of example 6, using BOPP film as upper substrate, PS plate as lower substrate. At room temperature, placing the "sandwich"-structure reactor under a 1000 w high-pressure mercury lamp (light intensity at λ=254 nm: 7.0 mw/cm$^2$) to receive irradiation for 10.0 minutes. Washing the modified BOPP film and PS plate with large amount of water first and then with anhydrous ethanol to remove the moisture attached on the surface of substrates, drying at room temperature to allow the anhydrous ethanol to completely volatilize.

The measurement of air/water contact angle of the substrate-BOPP film and PS plate etc. —before and after modification is the same as that of example 6. The results are shown in table 5. It is found that the compound 4 has good modification effect on surfaces of different substrates when different solvents are used based on the comparison of CA of the substrates before and after modification.

TABLE 5

Changes of water CA of the surfaces of compound 4 modified PS plate and BOPP film

| Solvent selected | | De-ionized water | NaCl water solution (0.02 wt %) | water/ethanol (50/50) | Water CA before modification |
|---|---|---|---|---|---|
| Water CA after modification | PS | 56.2° | 59.0° | 89.2° | 106.3° |
| | BOPP | 62.1° | 58.0° | 102.6° | 106.2° |

Example 9

Preparing a 0.58 mM modification solution of compound 4 by choosing ethanol as solvent. Making a "sandwich"-structure reactor by using the method of example 6, using BOPP film as upper substrate, and PC plate, PI film and PET film as lower substrate respectively. At room temperature, placing the "sandwich"-structure reactor under a 1000 w high-pressure mercury lamp (light intensity at λ=254 nm: 7.0 mw/cm$^2$) to receive irradiation for 10.0 minutes. Washing the modified PC plate, PI film and PET film with large amount of water first and then with anhydrous ethanol to remove the moisture attached on the surface of substrates, drying at room temperature to allow the anhydrous ethanol to completely volatilize.

The measurement of air/water contact angle of the substrate—PC plate, PI film and PET film etc. —before and after modification is the same as that of example 6. The results are shown in table 6. It is found that the compound 4 exerts a certain degree of modification effect on surfaces of different substrates based on the comparison of CA of the substrates before and after modification.

TABLE 6

Comparison of water CA of different substrates before and after modification with compound 4

| | PC | PI | PET |
|---|---|---|---|
| Before modification | 88.1° | 69.5° | 76.3° |
| After modification | 72.6° | 59.4° | 54.8° |

Example 10

Dissolving compound 7 in a 0.1 M LiOH water solution to prepare a 5.0 mM modification solution, two-fold dilute to obtain a series of modification solutions, removing the oxygen in each solution by passing nitrogen gas for 10 minutes. Make a "sandwich"-structure reactor by using the method of example 6, using BOPP film as upper and lower substrates. The irradiation lasts for 10 minutes by following the same method of UV radiation modification as in example 7. Washing the modified BOPP film with deionized water, and then immersing it in 100 mL of crystal violet water solution at a concentration of 0.15 mg/mL, incubating in a 22-23° C. oven for 30 minutes. Taking out, washing the surface of the BOPP film with deionized water, and then drying it in the 22-23° C. oven.

Taking the 5.0 mM modification solution as basis, changing the irradiation duration to 0.5, 2.0, 5.0, 7.0 and 10.0 minutes respectively to carry out surface treatment of BOPP film. The method of UV irradiation modification, post-treatment and crystal violet adsorption are the same as above.

Figure 4:
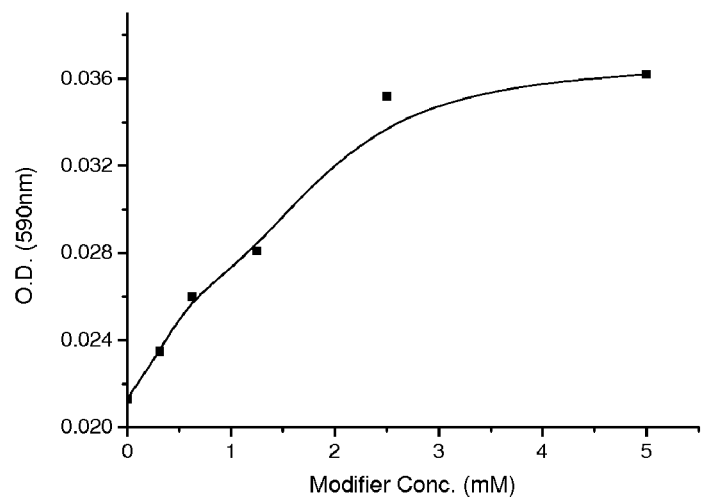
Figure 5:
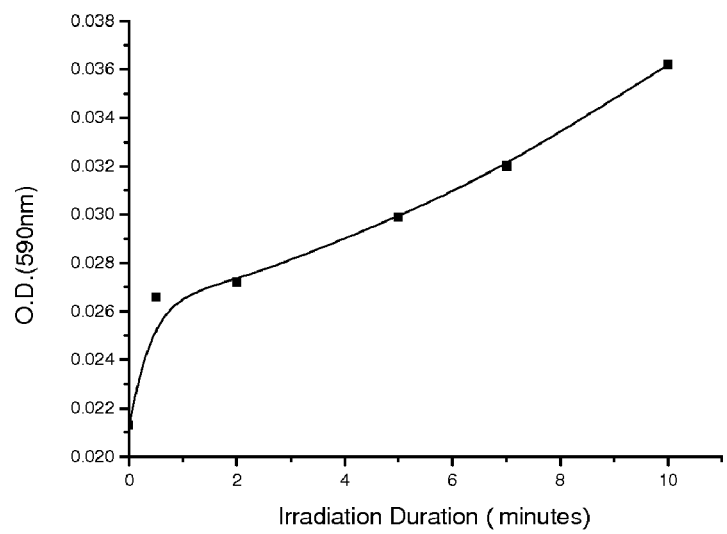

Measuring the crystal violet adsorptive effect of the modified BOPP film with a GBC Cintra 20 UV-Vis Spectrophometer (Australia). The results are shown in FIG. 4 and FIG. 5. As shown in the FIG. 4, the surface modification effect of BOPP film increases as the increase of the concentration of compound 7; as shown in the FIG. 5, prolonging irradiation duration is beneficial for improving the surface modification effect of compound 7 for BOPP film.

The invention claimed is:
1. A method for modifying surfaces of polymer materials, the method comprising the steps of: introducing functional group L onto the surface of a polymer material P by a photochemical reaction of a photosensitive group X under UV irradiation, wherein the photosensitive group X comprises at least one xanthone unit;
  wherein a molecule X-L and/or a molecule X-S-L are introduced onto the surface of the polymer material P, wherein X represents a photosensitive group comprising at least one xanthone unit, L represents a functional group, and S represents a linker;
  wherein the linker S is selected from: substituted or unsubstituted and/or functional group interrupted $C_{1-20}$ hydrocarbyl groups, polyethylene glycol, oligo/poly-amides, oligosaccharides, oligo/poly-phosphate esters or phosphate salts, oligo/poly-sulfamides/sulphonic acid esters, and a combination of above-mentioned units;
  wherein the photosensitive group X is originated from substituted mono-xanthone as shown in formula I:

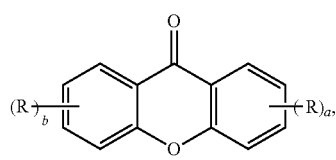

Formula I wherein R independently represents a substituents on the corresponding ring, a and b are independently selected from integers of 0-3, and a+b≧1;
  wherein the substituent R is selected from a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units.
2. The method of claim 1, further comprising the steps of: synthesizing the molecule X-L or X-S-L; and then having the molecule X-L or X-S-L photochemically reacted with the surface of polymer material P by UV irradiation, thereby introducing the molecule X-L or X-S-L onto the surface of the polymer material P to form a P-X-L or P-X-S-L.

3. The method of claim 2, comprising the steps of:
   A. synthesizing the molecule X-S-L or X-L;
   B. mixing the molecule X-S-L or X-L with a solvent to form a modification solution containing the molecule X-S-L or X-L;
   C. forming a modification solution layer on the surface of the modified polymer material P;
   D. radiating the surface of the polymer material P having the modification solution layer with ultraviolet light so as to introduce the molecule X-S-L or X-L onto the surface.

4. The method of claim 3, wherein the molecule X-S-L is synthesized by a way selected from:
   (1) a group X reacts with units $S_i$ that constitutes linker S stepwise till linker S reaches a desired length, to obtain an X-S, which is then linked with a group L to obtain an X-S-L;
   (2) units $S_i$ that constitute linker S react with each other to obtain linker S meeting the length requirement, and then the linker S reacts with a group X to obtain an X-S, which is then linked with a group L to obtain an X-S-L;
   (3) units $S_i$ that constitute linker S react with each other to obtain linker S meeting the length requirement, and then the linker S reacts with a group L to obtain an S-L, which is then linked with a group X to obtain an X-S-L;
   (4) a group L reacts with units $S_i$ that constitutes linker S stepwise till linker S reaches a desired length, to obtain an S-L, which is then linked with a group X to obtain an X-S-L.

5. The method of claim 1, comprising: having a photosensitive group X photochemically reacted with the surface of the polymer material P with UV irradiation to form P-X, and synthesizing a molecule S-L independently, and then linking molecule S-L with the surface of the polymer material P where P-X has been formed, with photochemical or thermochemical reaction, thereby forming P-X-S-L.

6. The method of claim 1, comprising: synthesizing a molecule X-S, and then linking molecule X-S to the surface of the polymer material P by photochemical reaction to form P-X-S, followed by linking a functional group L to the surface of the polymer material P where the P-X-S has been formed, with photochemical or thermochemical reaction, thereby forming P-X-S-L.

7. The method of claim 1, comprising: fixing a photosensitive group X onto the surface of the polymer material P by photochemical reaction to form P-X, and then optionally linking a linker S through photochemical or thermochemical reaction with the photosensitive group X to form P-X-S, and subsequently linking a functional group L with the photosensitive group X that has been fixed onto the surface of the polymer material P and has been optionally linked with the linker S, by photochemical or thermochemical reaction, thereby introducing a molecule X-L or X-S-L onto the surface of the polymer material P to form P-X-L or a P-X-S-L.

8. The method of claim 1, wherein the thermosensitive functional groups are selected from carboxyl groups, hydroxyl groups, amine groups, thiol groups, sulfonic acid groups, halogen atoms, ester groups, acyl halide groups, acid hydrazide groups, semicarbazide groups, thiosemicarbazide groups, aldehyde groups, and ketone groups.

9. The method of claim 8, wherein before introducing molecule X-L and/or X-S-L onto the surface of the polymer material P, a linker S' is fixed onto the surface of the polymer material P to be modified, through photochemical or thermochemical reaction, to form a P-S'.

10. The method of claim 1, wherein the acyclic hydrocarbyl group is $C_{1-18}$ acyclic hydrocarbyl group.

11. The method of claim 10, wherein the acyclic hydrocarbyl group is $C_{1-8}$ alkyl or $C_{2-8}$ unsaturated hydrocarbyl group.

12. The method of claim 10, wherein the acyclic hydrocarbyl group is $C_{1-5}$ alkyl or $C_{2-5}$ unsaturated hydrocarbyl group.

13. The method of claim 10, wherein the acyclic hydrocarbyl groups is substituted and/or interrupted by one or more functional groups selected from carboxyl groups, hydroxyl groups, amine groups, imine groups, thiol groups, sulfonic acid groups, halogen atoms, ester functional groups, acyl halide groups, acid hydrazide groups, semicarbazide groups, thiosemicarbazide groups, aldehyde groups, ketone groups, epoxide groups, ether groups, thioether groups, carbonyl groups, sulfonyl groups, sufinyl groups, nitro groups, nitrile groups, phosphoryl functional groups, furan functional groups, carbohydrate functional groups and acyl functional groups.

14. The method of claim 13, wherein before introducing molecule X-L and/or X-S-L onto the surface of the polymer material P, a linker S' is fixed onto the surface of the polymer material P to be modified, through photochemical or thermochemical reaction, to form a P-S'.

15. The method of claim 1, wherein the rings in the ring structures is saturated cyclic hydrocarbons, unsaturated cyclic hydrocarbons, saturated heterocyclic hydrocarbons or unsaturated heterocyclic hydrocarbons having 5 to 6 carbon atoms.

16. The method of claim 15, wherein the ring atoms in the ring structures comprises one or more hetero atoms selected from O, N, and S.

17. The method of claim 15, wherein the rings in the ring structures are selected from cyclopentane, cyclohexane, cyclopentanone, cyclohexanone, benzene, cyclopentene, cyclohexene, cyclohexadiene, oxocyclopentane, oxocyclohexane, piperidine, dioxocyclopentane, dioxocyclohexane, thiocyclopentane, thiocyclohexane, caprolactam, caprolactone, oxocyclopentanone, oxocyclohexanone, oxocyclohexene, thiocyclohexene, furan ring, pyrrole ring, thiophene ring, pyridine, pyrimidine, imidazole, benzocyclohexanone, benzo-oxocyclohexanone, and oxocyclohexano-benzocyclohexanone.

18. The method of claim 17, wherein the ring structures are substituted by one or more functional groups selected from a $C_{1-18}$ acyclic hydrocarbyl group, halogen atoms, carboxyl groups, sulfonic acid groups, ester groups, nitro groups, acyl halide groups, amine groups, hydroxyl groups, amide groups, aldehyde groups, sulfonic acid groups, thiol groups, ketone groups, sulfonyl groups, and sufinyl groups.

19. The method of claim 18, wherein before introducing molecule X-L and/or X-S-L onto the surface of the polymer material P, a linker S' is fixed onto the surface of the polymer material P to be modified, through photochemical or thermochemical reaction, to form a P-S'.

20. The method of claim 1, wherein the $C_{1-20}$ hydrocarbyl group is substituted or unsubstituted and/or interrupted by one or more functional groups selected from carboxyl groups, hydroxyl groups, amine groups, imine groups, thiol groups, sulfonic acid groups, halogen atoms, ester functional groups, acyl halide groups, acid hydrazide groups, semicarbazide groups, thiosemicarbazide groups, aldehyde groups, ketone groups, epoxide groups, ether groups, thio-ether groups, carbonyl, sulfonyl groups, sulfinyl groups, nitro groups, nitrile groups, phosphoryl functional groups, furan functional groups, carbohydrate functional groups and acyl functional groups.

21. The method of claim 20, wherein the length of linker S should be no more than 40 nm.

22. The method of claim 21, wherein before introducing molecule X-L and/or X-S-L onto the surface of the polymer material P, a linker S' is fixed onto the surface of the polymer material P to be modified, through photochemical or thermochemical reaction, to form a P-S'.

23. The method of claim 1, wherein the functional group L is selected from —COOH, —COOR', —COO⁻M⁺, —SO₃H, —SO₃R', —SO₃⁻M⁺, —COX, —CONHNH₂, —NH-CONHNH₂, —NHCSNHNH₂, —CN, —CHO, —COR', —OH, —SH, —SSR', amine groups, ammonium salt groups, hydrazine groups, —OR', —SR', epoxide groups, —X, —NO₂, —R', —R'X$_n$, where R' represents hydrocarbyl groups, M⁺ represents monovalent metal ions, or NH₄⁺, or X represents halogen atoms, n≦(2×the number of carbon atoms in the R'+1), and/or the functional group L are derived from phosphorylcholines, heterocyclic rings, metal complexes, theophyllines, onium salts, carbohydrates, antibiotics, vitamins, toxins, herbicides, pesticides, steroids, polypeptides, nucleotides, polypeptide nucleic acids and haptens.

24. The method of claim 23, wherein before introducing molecule X-L and/or X-S-L onto the surface of the polymer material P, a linker S' is fixed onto the surface of the polymer material P to be modified, through photochemical or thermochemical reaction, to form a P-S'.

25. The method of claim 1, wherein the polymer material is selected from polyolefins, rubbers, polyurethanes, polyamides, polycarbonates, polyimids, polyesters, fluoro-resins, polyethers, polyvinyl alcohols, polyvinyl acetate, polyacrylates, biopolymers, or the blends, composites thereof.

26. The method of claim 25, wherein the polymer material is selected form: polyethylene, polypropylene, polystyrene, polyvinyl chloride, styrene butadiene rubber, butadiene-acrylonitrile rubber, SBS, ethylene propylene rubber, chloroprene rubber, silicon rubber, chlorohydrin rubber; polycaprolactam, polyhexamethylene carbonate, polyethylene terephthalate, polycaprolactone, polytetrafluoroethylene, tetrafluoroethylene-hexafluoropropylene copolymer, polyphenylene oxide, polyethylene glycol, polyvinyl alcohols, polymethyl methacrylate, chitin, chitosan, poly-amino acids, poly-lactic acids; or the blends, composites thereof.

27. The method of claim 26, wherein before introducing molecule X-L and/or X-S-L onto the surface of the polymer material P, a linker S' is fixed onto the surface of the polymer material P to be modified, through photochemical or thermochemical reaction, to form a P-S'.

28. A modification compound used for ultraviolet light assisted polymer material surface modification method, having a photosensitive group X and a functional group L, wherein the photosensitive group X comprises at least one xanthone unit;
wherein the structure of the compound is selected from X-L and X-S-L, wherein X is a photosensitive group comprising at least one xanthone unit, L is a functional group, and S is a linker;
wherein the linker S is selected from: substituted or unsubstituted and/or functional groups interrupted $C_{1-20}$ hydrocarbyl groups, polyethylene glycol, oligo/polyamides, oligosaccharides, oligo/poly-phosphate esters, oligo/poly-sulfamides/sulphonic acid esters, and a combination of above-mentioned units;
wherein the photosensitive group X is originated from substituted mono-xanthone as shown in formula I,

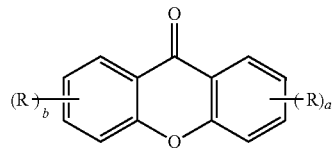

Formula I wherein R independently represents a substituents on the corresponding ring, a and b are independently selected from integers of 0-3, and a+b≧1;
wherein the substituent R is selected from a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units.

29. The modification compound of claim 28, wherein the compound having structure of X-S-L is synthesized by a way selected from:
(1) a group X reacts with units $S_i$ that constitutes linker S stepwise till linker S reaches a desired length, to obtain an X-S, which is then linked with a group L to obtain an X-S-L;
(2) units $S_i$ that constitute linker S react with each other to obtain linker S meeting the length requirement, and then the linker S reacts with a group X to obtain an X-S, which is then linked with a group L to obtain an X-S-L;
(3) units $S_i$ that constitute linker S react with each other to obtain linker S meeting the length requirement, and then the linker S reacts with a group L to obtain an S-L, which is then linked with a group X to obtain an X-S-L;
(4) a group L reacts with units $S_i$ that constitutes linker S stepwise till linker S reaches a desired length, to obtain an S-L, which is then linked with a group X to obtain an X-S-L.

30. The modification compound of claim 28, wherein the thermosensitive functional groups are selected from carboxyl groups, hydroxyl groups, amine groups, thiol groups, sulfonic acid groups, halogen atoms, ester groups, acyl halide groups, acid hydrazide groups, semicarbazide groups, thiosemicarbazide groups, aldehyde groups, and ketone groups.

31. The modification compound of claim 28, wherein the acyclic hydrocarbyl group is $C_{1-18}$ acyclic hydrocarbyl group.

32. The modification compound of claim 31, wherein the acyclic hydrocarbyl group is $C_{1-8}$ alkyl or $C_{2-8}$ unsaturated hydrocarbyl group.

33. The modification compound of claim 31, wherein the acyclic hydrocarbyl group is $C_{1-5}$ alkyl or $C_{2-5}$ unsaturated hydrocarbyl group.

34. The modification compound of claim 28, wherein the acyclic hydrocarbyl groups is substituted and/or interrupted by one or more functional groups selected from carboxyl groups, hydroxyl groups, amine groups, imine groups, thiol groups, sulfonic acid groups, halogen atoms, ester functional groups, acyl halide groups, acid hydrazide groups, semicarbazide groups, thiosemicarbazide groups, aldehyde groups, ketone groups, epoxide groups, ether groups, thioether groups, carbonyl groups, sulfonyl groups, sufinyl groups, nitro groups, nitrile groups, phosphoryl functional groups, furan functional groups, carbohydrate functional groups and acyl functional groups.

35. The modification compound of claim 28, wherein the rings in the ring structures is saturated cyclic hydrocarbons, unsaturated cyclic hydrocarbons, saturated heterocyclic hydrocarbons or unsaturated heterocyclic hydrocarbons having 5 to 6 carbon atoms.

36. The modification compound of claim 35, wherein the ring atoms in the ring structures comprises one or more hetero atoms selected from O, N, and S.

37. The modification compound of claim 35, wherein the rings in the ring structures are selected from cyclopentane, cyclohexane, cyclopentanone, cyclohexanone, benzene, cyclopentene, cyclohexene, cyclohexadiene, oxocyclopentane, oxocyclohexane, piperidine, dioxocyclopentane, dioxocyclohexane, thiocyclopentane, thiocyclohexane, caprolactam, caprolactone, oxocyclopentanone, oxocyclohexanone, oxocyclohexene, thiocyclohexene, furan ring, pyrrole ring, thiophene ring, pyridine, pyrimidine, imidazole, benzocyclohexanone, benzo-oxocyclohexanone, and oxocyclohexano-benzocyclohexanone.

38. The modification compound of claim 37, wherein the ring structures are substituted by one or more functional groups selected from a $C_{1-18}$ acyclic hydrocarbyl group, halogen atoms, carboxyl groups, sulfonic acid groups, ester groups, nitro groups, acyl halide groups, amine groups, hydroxyl groups, amide groups, aldehyde groups, sulfonic acid groups, thiol groups, ketone groups, sulfonyl groups, and sufinyl groups.

39. The modification compound of claim 28, wherein the $C_{1-20}$ hydrocarbyl group is substituted or unsubstituted and/or interrupted by one or more functional groups selected from carboxyl groups, hydroxyl groups, amine groups, imine groups, thiol groups, sulfonic acid groups, halogen atoms, ester functional groups, acyl halide groups, acid hydrazide groups, semicarbazide groups, thiosemicarbazide groups, aldehyde groups, ketone groups, epoxide groups, ether groups, thio-ether groups, carbonyl, sulfonyl groups, sulfinyl groups, nitro groups, nitrile groups, phosphoryl functional groups, furan functional groups, carbohydrate functional groups and acyl functional groups.

40. The modification compound of claim 39, wherein the length of linker S should be no more than 40 nm.

41. The modification compound of claim 28, wherein the functional group L is selected from —COOH, —COOR', —COO⁻M⁺, —SO₃H, —SO₃R', —SO₃⁻M⁺, —COX, —CONHNH₂, —NHCONHNH₂, —NHCSNHNH₂, —CN, —CHO, —COR', —OH, —SH, —SSR', amine groups, ammonium salt groups, hydrazine groups, —OR', —SR', epoxide groups, —X, —NO₂, —R', —R'X$_n$, where R' represents hydrocarbyl groups, M⁺ represents monovalent metal ions, or NH₄⁺, or X represents halogen atoms, n≦(2×the number of carbon atoms in the R'+1), and/or the functional group L are derived from phosphorylcholines, heterocyclic rings, metal complexes, theophyllines, onium salts, carbohydrates, antibiotics, vitamins, toxins, herbicides, pesticides, steroids, polypeptides, nucleotides, polypeptide nucleic acids and haptens.

42. The modification compound of claim 40, wherein the functional group L is selected from —COOH, —COOR', —COO⁻M⁺, —SO₃H, —SO₃R', —SO₃⁻M⁺, —COX, —CONHNH₂, —NHCONHNH₂, —NHCSNHNH₂, —CN, —CHO, —COR', —OH, —SH, —SSR', amine groups, ammonium salt groups, hydrazine groups, —OR', —SR', epoxide groups, —X, —NO₂, —R', —R'X$_n$, where R' represents hydrocarbyl groups, M⁺ represents monovalent metal ions, or NH₄⁺, or X represents halogen atoms, n≦(2×the number of carbon atoms in the R'+1), and/or the functional group L are derived from phosphorylcholines, heterocyclic rings, metal complexes, theophyllines, onium salts, carbohydrates, antibiotics, vitamins, toxins, herbicides, pesticides, steroids, polypeptides, nucleotides, polypeptide nucleic acids and haptens.

43. An article having polymer material surfaces formed through modification with the method according to claim 1.

44. A modification compound used for ultraviolet light assisted polymer material surface modification method, having a photosensitive group X and a functional group L, wherein the photosensitive group X comprises at least one xanthone unit, and is originated from substituted mono-xanthone as shown in formula I,

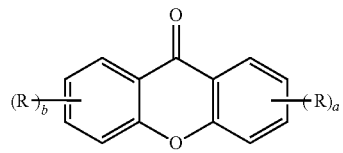

Formula I wherein R independently represents a substituent on the corresponding ring, a and b are independently selected from integers of 0-3, and a+b≧1, wherein the substituent R is selected from a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units.

45. A method for modifying surfaces of polymer materials, the method comprising the steps of:

introducing functional group L onto the surface of a polymer material P by a photochemical reaction of a photosensitive group X under UV irradiation, wherein the photosensitive group X comprises at least one xanthone unit, wherein a molecule X-L and/or a molecule X-S-L are introduced onto the surface of the polymer material P, wherein X represents a photosensitive group comprising at least one xanthone unit, L represents a functional group, and S represents a linker; and having a photosensitive group X photochemically reacted with the surface of the polymer material P with UV irradiation to form P-X, and synthesizing a molecule S-L independently, and then linking molecule S-L with the surface of the polymer material P where P-X has been formed, with photochemical or thermochemical reaction, thereby forming P-X-S-L;

wherein the photosensitive group X is originated from substituted mono-xanthone as shown in formula I,

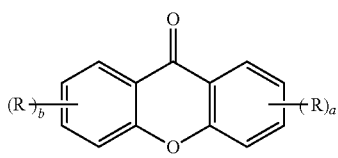

Formula I wherein R independently represents a substituents on the corresponding ring, a and b are independently selected from integers of 0-3, and a+b≧1;

wherein the substituent R is selected from a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units.

46. A method for modifying surfaces of polymer materials, the method comprising the steps of:

introducing functional group L onto the surface of a polymer material P by a photochemical reaction of a photosensitive group X under UV irradiation, wherein the photosensitive group X comprises at least one xanthone unit, wherein a molecule X-L and/or a molecule X-S-L are introduced onto the surface of the polymer material P, wherein X represents a photosensitive group comprising at least one xanthone unit, L represents a functional group, and S represents a linker; and synthesizing a molecule X-S, and then linking molecule X-S to the surface of the polymer material P by photochemical reaction to form P-X-S, followed by linking a functional group L to the surface of the polymer material P where the P-X-S has been formed, with photochemical or thermochemical reaction, thereby forming P-X-S-L;

wherein the photosensitive group X is originated from substituted mono-xanthone as shown in formula I,

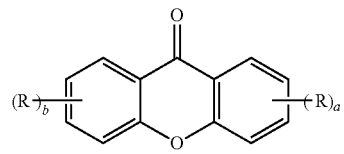

Formula I wherein R independently represents a substituents on the corresponding ring, a and b are independently selected from integers of 0-3, and a+b≧1;

wherein the substituent R is selected from a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units.

47. A method for modifying surfaces of polymer materials, the method comprising the steps of:

introducing functional group L onto the surface of a polymer material P by a photochemical reaction of a photosensitive group X under UV irradiation, wherein the photosensitive group X comprises at least one xanthone unit, wherein a molecule X-L and/or a molecule X-S-L are introduced onto the surface of the polymer material P, wherein X represents a photosensitive group comprising at least one xanthone unit, L represents a functional group, and S represents a linker; and fixing a photosensitive group X onto the surface of the polymer material P by photochemical reaction to form P-X, and then optionally linking a linker S through photochemical or thermochemical reaction with the photosensitive group X to form P-X-S, and subsequently linking a functional group L with the photosensitive group X that has been fixed onto the surface of the polymer material P and has been optionally linked with the linker S, by photochemical or thermochemical reaction, thereby introducing a molecule X-L or X-S-L onto the surface of the polymer material P to form P-X-L or a P-X-S-L;

wherein the photosensitive group X is originated from substituted mono-xanthone as shown in formula I,

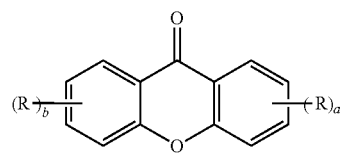

Formula I wherein R independently represents a substituents on the corresponding ring, a and b are independently selected from integers of 0-3, and a+b≧1;

wherein the substituent R is selected from a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units.

48. A method for modifying surfaces of polymer materials, the method comprising the steps of:

introducing functional group L onto the surface of a polymer material P by a photochemical reaction of a photosensitive group X under UV irradiation, wherein the photosensitive group X comprises at least one xanthone unit;

wherein a molecule X-L and/or a molecule X-S-L are introduced onto the surface of the polymer material P, wherein X represents a photosensitive group comprising at least one xanthone unit, L represents a functional group, and S represents a linker; and wherein before introducing molecule X-L and/or X-S-L onto the surface of the polymer material P, a linker S' is fixed onto the surface of the polymer material P to be modified, through photochemical or thermochemical reaction, to form a P-S'.

49. A method for modifying surfaces of polymer materials, the method comprising the steps of:

introducing functional group L onto the surface of a polymer material P by a photochemical reaction of a photosensitive group X under UV irradiation, wherein the photosensitive group X comprises at least one xanthone unit and is originated from substituted mono-xanthone as shown in formula I:

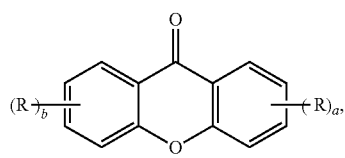

Formula I wherein R independently represents a substituent on the corresponding ring, a and b are independently selected from integers of 0-3, and a+b≧1, and R is selected from a thermosensitive functional group, an acyclic hydrocarbyl group that is substituted or unsubstituted and/or interrupted by a functional group, a substituted or unsubstituted independent ring structure relative to the mono-xanthone units, or a substituted or unsubstituted fused ring formed together with the ring atoms of the mono-xanthone units.

50. A method for modifying surfaces of polymer materials, the method comprising the steps of: introducing functional group L onto the surface of a polymer material P by a photochemical reaction of a photosensitive group X under UV irradiation, wherein the photosensitive group X comprises at least one xanthone unit;

wherein a molecule X-L and/or a molecule X-S-L are introduced onto the surface of the polymer material P, wherein X represents a photosensitive group comprising at least one xanthone unit, L represents a functional group, and S represents a linker;

wherein the linker S is selected from: substituted or unsubstituted and/or functional group interrupted $C_{1-20}$ hydrocarbyl groups, polyethylene glycol, oligo/poly-amides, oligosaccharides, oligo/poly-phosphate esters or phosphate salts, oligo/poly-sulfamides/sulphonic acid esters, and a combination of above-mentioned units;

wherein before introducing molecule X-L and/or X-S-L onto the surface of the polymer material P, a linker S' is fixed onto the surface of the polymer material P to be modified, through photochemical or thermochemical reaction, to form a P-S'.

* * * * *